(12) United States Patent
Michaelis et al.

(10) Patent No.: US 6,900,204 B2
(45) Date of Patent: May 31, 2005

(54) ANTIMICROBIAL AGENTS AND USES THEREOF

(75) Inventors: Arthur F. Michaelis, Devon, PA (US); Hawkins V. Maulding, Mendham, NJ (US)

(73) Assignee: ActivBiotics, Inc., Lexington, MA (US)

( * ) Notice: Subject to any disclaimer, the term of this patent is extended or adjusted under 35 U.S.C. 154(b) by 6 days.

(21) Appl. No.: 10/237,800

(22) Filed: Sep. 6, 2002

(65) Prior Publication Data

US 2003/0105086 A1 Jun. 5, 2003

Related U.S. Application Data

(60) Provisional application No. 60/317,615, filed on Sep. 6, 2001.

(51) Int. Cl.[7] .................... C07D 498/04; C07D 513/04; A61K 31/5365; A61K 31/542; A61P 31/04
(52) U.S. Cl. ........................ 514/229.5; 544/99; 544/14; 544/52; 544/105; 544/392
(58) Field of Search .......................... 544/99; 514/229.5

(56) References Cited

U.S. PATENT DOCUMENTS

| | | | |
|---|---|---|---|
| 4,690,919 A | 9/1987 | Yamane et al. | 514/183 |
| 4,859,661 A | 8/1989 | Kano et al. | 514/183 |
| 4,859,667 A | 8/1989 | Lau et al. | 514/224.5 |
| 4,983,602 A | 1/1991 | Yamane et al. | 514/229.5 |
| 5,786,349 A | 7/1998 | Yamashita et al. | 514/183 |
| 5,981,522 A | 11/1999 | Yamashita et al. | 514/224.5 |

OTHER PUBLICATIONS

Bartolucci et al., "Structure–activity relationships in open ansa–chain rifamycin S derivatives as inhibitors of HIV–1 reverse transcriptase" *Farmaco* 50:587 (1995).

Yamane et al., "Synthesis and biological activity of 3'-hydroxy-5'-aminobenzoxazinorifamycin derivatives" *Chem. Pharm. Bul.* (Tokyo) 41:148 (1993).

*Primary Examiner*—Mark L. Berch
*Assistant Examiner*—Kahsay Habte
(74) *Attorney, Agent, or Firm*—Clark & Elbing LLP

(57) ABSTRACT

The invention features compounds that act as antimicrobial agents and/or antimicrobial enhancer agents, compositions that include the antimicrobial enhancer agents of the invention, and methods for treating microbial infections using those compositions.

36 Claims, 4 Drawing Sheets

ANTIMICROBIAL AGENTS AND USES THEREOF

CROSS REFERENCE TO RELATED APPLICATIONS

This application claims benefit of the filing date of U.S. Ser. No. 60/317,615, filed Sep. 6, 2001, hereby incorporated by reference.

BACKGROUND OF THE INVENTION

The invention relates to the field of antimicrobial agents and to methods for potentiating antimicrobial agents.

The benefit from use of antibiotics as a means of treating infections has been increasingly compromised by the development of resistant strains of microorganisms. One approach taken by manufacturers of antimicrobial agents is to devise agents to which the organisms are not resistant. Because considerable time and resources have been spent on the development of current antimicrobial agents, it is desirable to develop antimicrobial enhancer agents that, when administered with an antimicrobial agent, render the otherwise resistant microbes sensitive to the antimicrobial agent.

SUMMARY OF THE INVENTION

The invention features compounds that act as antimicrobial agents and/or as antimicrobial enhancer agents. As antimicrobial enhancers, these agents are useful for treating microbial infections when co-administered with an antimicrobial agent. Thus, the invention also features compositions that include the compounds of the invention in combination with one or more antimicrobial agents, and methods for treating microbial infections using those compositions.

In a first aspect, the invention features a compound having the chemical structure of formula (I) below:

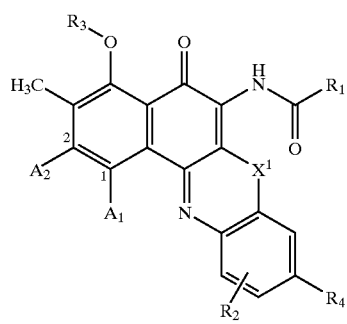

I

In formula I, $A_1$ and $A_2$ combine to form a fused ring described by formulas:

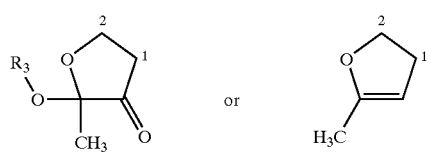

$X^1$ represents an oxygen atom or a sulfur atom, $R_1$ represents H, $C_{1-6}$ alkyl, $C_{2-6}$ alkenyl, $C_{2-6}$-alkynyl, aryl, or heteroalkyl, $R_2$ represents $OR_3$, $SR_3$, a hydrogen atom, or an alkyl group having 1 to 3 carbon atoms, each $R_3$, independently, represents H, $C_{1-6}$ alkyl, $C_{2-6}$ alkenyl, $C_{2-6}$-alkynyl, acyl, aryl, heteroalkyl, $S(O)_{1-2}$—$C_{1-6}$ alkyl, $S(O)_{1-2}$-aryl, $S(O)_{1-2}$—$C_{2-6}$ alkenyl, or $S(O)_{1-2}$—$C_{2-6}$-alkynyl, and $R_4$ represents a group expressed by the formula:

wherein each of $R_5$ and $R_6$ is, independently, an alkyl group having 1 to 7 carbon atoms, or $R_5$ and $R_6$ combine to form a 3–8 membered cyclic system, or $R_4$ represents a group expressed by the formula:

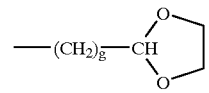

in which g represents an integer between 1 and 3;

or $R_4$ represents a group expressed by the formula:

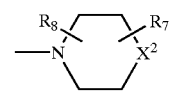

wherein each of $R_7$ and $R_8$ is, independently, a hydrogen atom or an alkyl group having 1 to 3 carbon atoms, $X^2$ represents an oxygen atom, a sulfur atom, a carbonyl group, or $X^2$ represents a group expressed by the formula:

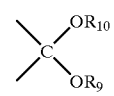

in which each of $R_9$ and $R_{10}$ is, independently, a hydrogen atom, or an alkyl group having 1 to 3 carbon atoms, or $R_9$ and $R_{10}$, in combination with each other, represent —$(CH_2)_k$— in which k represents an integer between 1 and 4;

or $X^2$ represents a group expressed by the formula:

in which m represents 0 or 1, $R_{11}$ represents a hydrogen atom, an alkyl group having 1 to 6 carbon atoms, or —$(CH_2)_n X^3$ in which n represents an integer between 1 and 4, and $X^3$ represents a halogen atom, an alkoxy group having 1 to 3 carbon atoms, a vinyl group, or an ethynyl group, or $X^2$ represents a group expressed by the formula:

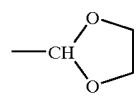

In one embodiment of the first aspect, the compound is described by formula (II) below:

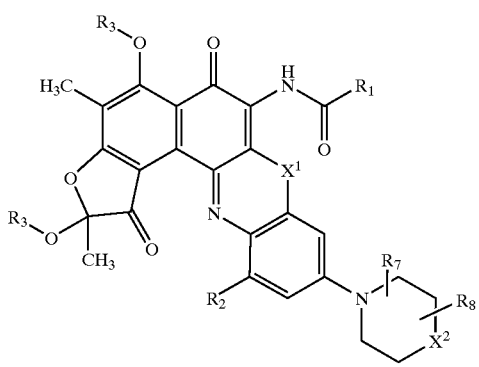

II wherein $R_1$, $R_2$, $R_3$, $R_7$, and $R_8$ are as defined above, and $X^2$ represents a group expressed by the formula:

in which m represents 0 or 1, and $R_{11}$ represents a hydrogen atom, an alkyl group having 1 to 6 carbon atoms, or $-(CH_2)_n X^3$ in which n represents an integer between 1 and 4, and $X^3$ represents a halogen atom, an alkoxy group having 1 to 3 carbon atoms, a vinyl group, or an ethynyl group.

For example, the compound may have one of the chemical structures below:

A-1

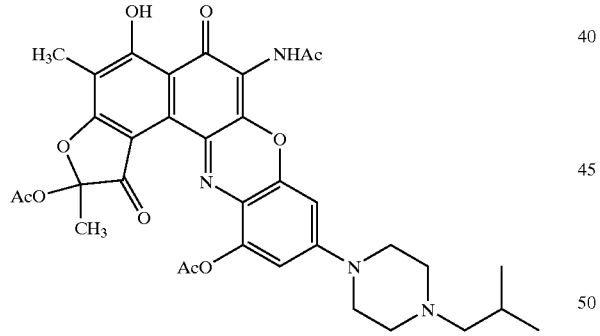

A-2

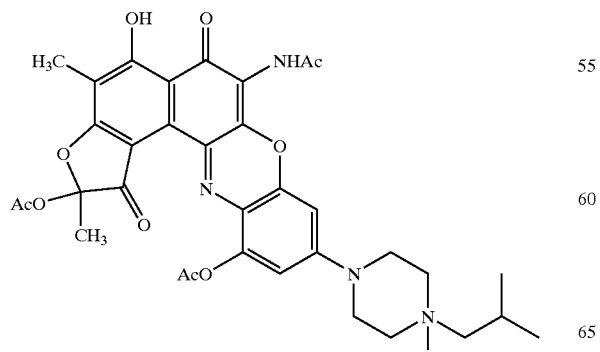

A-3

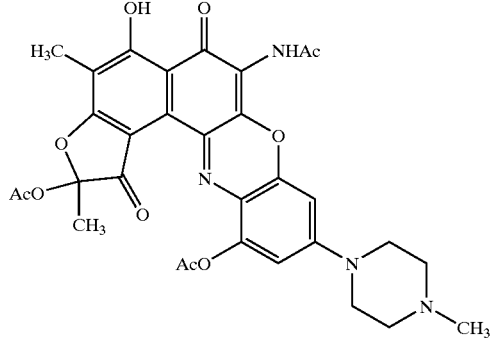

A-4

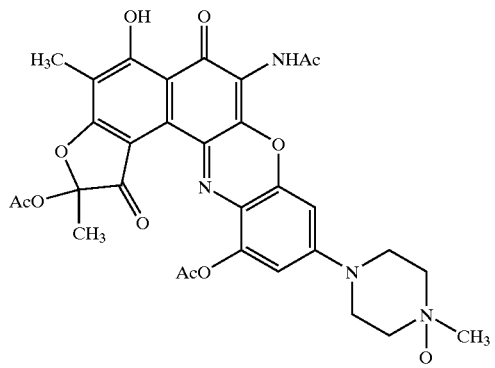

A-5

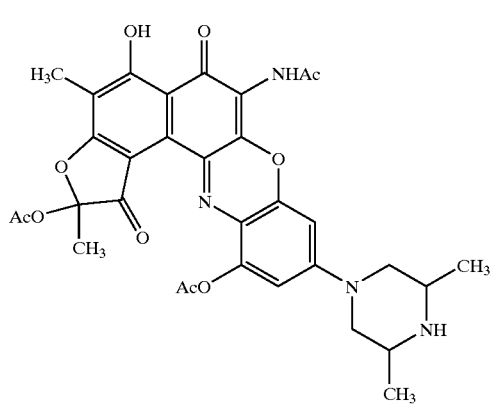

A-6

In another embodiment of the first aspect, the compound is described by formula (III) below:

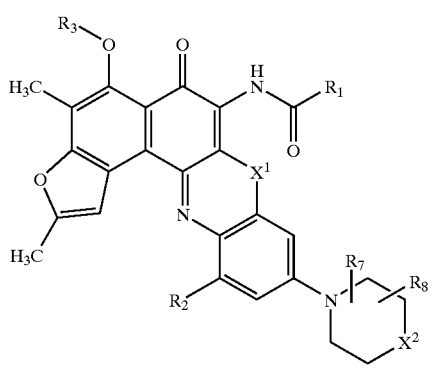

III wherein $R_1$, $R_2$, $R_3$, $R_7$, and $R_8$ are as defined above, and $X^2$ represents a group expressed by the formula:

in which m represents 0 or 1, and $R_{11}$ represents a hydrogen atom, an alkyl group having 1 to 6 carbon atoms, or —$(CH_2)_nX^3$ in which n represents an integer between 1 and 4, and $X^3$ represents a halogen atom, an alkoxy group having 1 to 3 carbon atoms, a vinyl group, or an ethynyl group.

For example, the compound may have one of the chemical structures below:

B-1

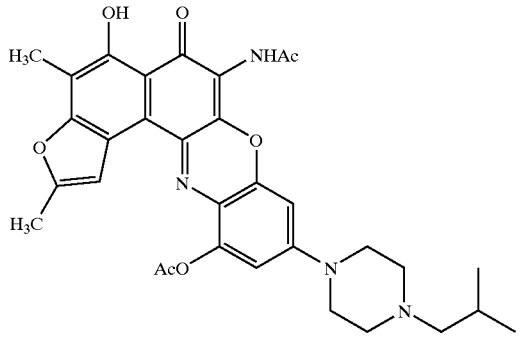

B-2

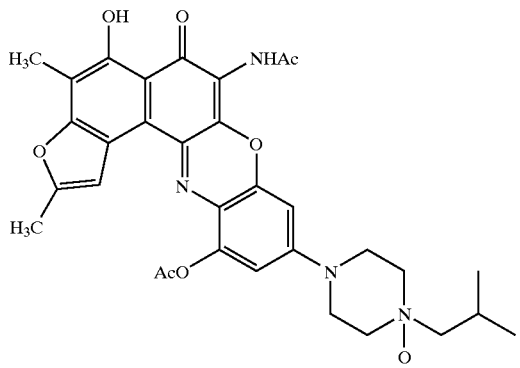

B-3

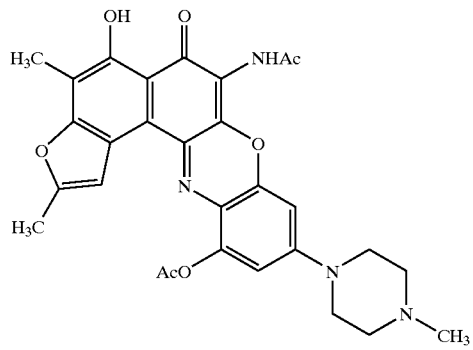

B-4

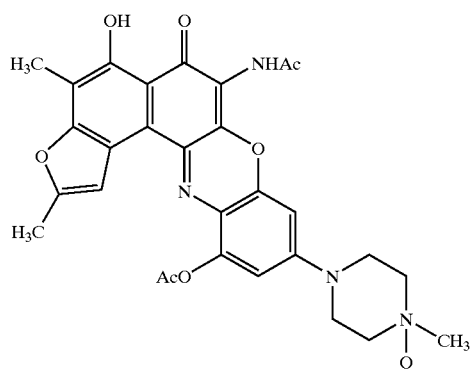

B-5

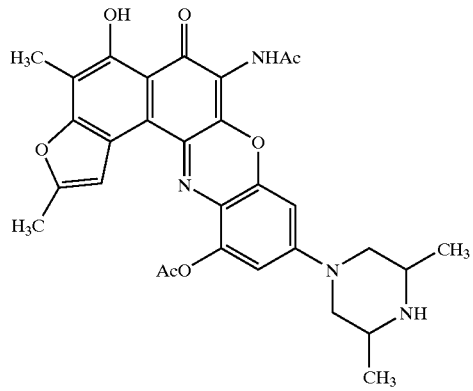

B-6

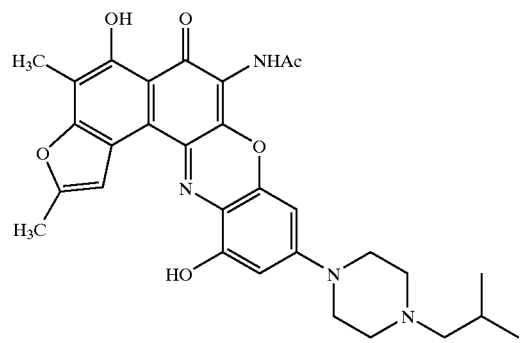

In a second aspect, the invention features a compound having the chemical structure of formula (IV) below:

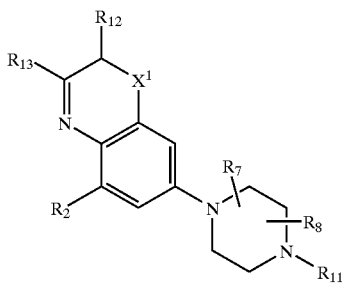

(IV)

wherein $X^1$ represents an oxygen atom or a sulfur atom, $R_2$ represents $OR_3$, $SR_3$, a hydrogen atom, or an alkyl group having 1 to 3 carbon atoms, each $R_3$, independently, represents H, $C_{1-6}$ alkyl, $C_{2-6}$ alkenyl, $C_{2-6}$-alkynyl, acyl, aryl, heteroalkyl, $S(O)_{1-2}$—$C_{1-6}$ alkyl, $S(O)_{1-2}$-aryl, $S(O)_{1-2}$—$C_{2-6}$ alkenyl, or $S(O)_{1-2}$—$C_{2-6}$-alkynyl, each of $R_7$ and $R_8$ is, independently, a hydrogen atom or an alkyl group having 1 to 3 carbon atoms, $R_{11}$ represents a hydrogen atom, an alkyl group having 1 to 6 carbon atoms, or —$(CH_2)_n X^3$ in which n represents an integer between 1 and 4, and $X^3$ represents a halogen atom, an alkoxy group having 1 to 3 carbon atoms, a vinyl group, or an ethynyl group; $R_{12}$ is H, O, $C_{1-6}$ alkyl, $C_{2-6}$ alkenyl, $C_{2-6}$ alkynyl, acyl, aryl, or heteroalkyl, and $R_{13}$ is H, $C_{1-6}$ alkyl, $C_{2-6}$ alkenyl, $C_{2-6}$ alkynyl, acyl, aryl, heteroalkyl, OH, SH, $OR_3$, or $SR_3$.

In various embodiments of the second aspect, $X^1$ is O, $R_2$ is H or $CH_3$, $R_{11}$ is a $C_{1-6}$ alkyl, $R_{12}$ is O, $CH_3$, or $C_6H_5$, and $R_{13}$ is $CH_3$, $C_6H_5$, $OCH_3$, $OCH_2C_6H_5$, or $OC_6H_5$. In particular embodiments, the compound has one of the chemical structures below:

C-1

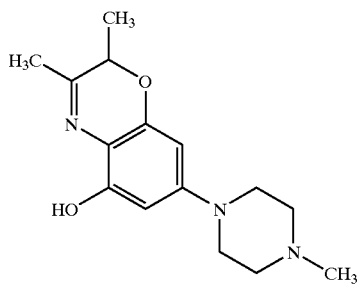

C-2

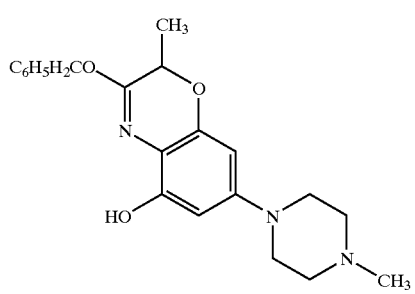

C-3

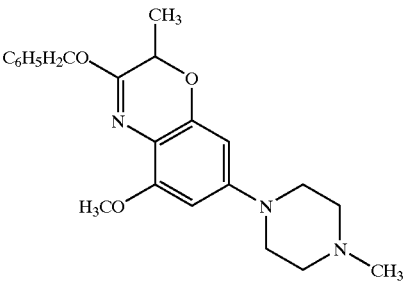

C-4

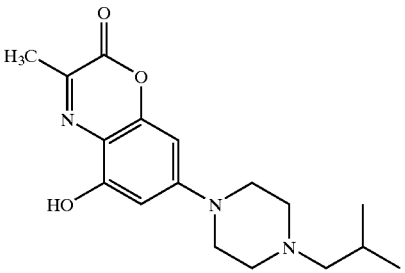

C-5

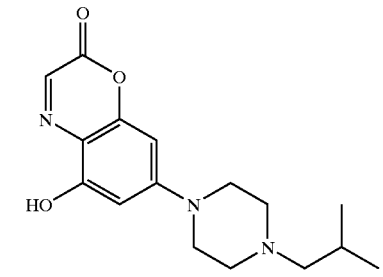

In a third aspect, the invention features a compound having the chemical structure of formula (V) below:

(V)

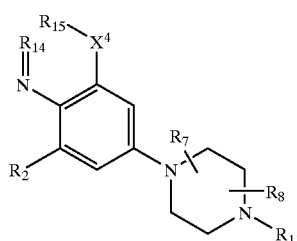

wherein $X^4$ represents an oxygen atom or a sulfur atom, $R_2$ represents $OR_3$, $SR_3$, a hydrogen atom, or an alkyl group having 1 to 3 carbon atoms, $R_3$ independently, represents H, $C_{1-6}$ alkyl, $C_{2-6}$ alkenyl, $C_{2-6}$-alkynyl, acyl, aryl, heteroalkyl, $S(O)_{1-2}$—$C_{1-6}$ alkyl, $S(O)_{1-2}$-aryl, $S(O)_{1-2}$—$C_{2-6}$ alkenyl, or $S(O)_{1-2}$—$C_{2-6}$-alkynyl, each of $R_7$ and $R_8$ is, independently, a hydrogen atom or an alkyl group having 1 to 3 carbon atoms $R_{11}$ represents a hydrogen atom, an alkyl group having 1 to 6 carbon atoms, or —$(CH_2)_n X^3$ in which n represents an integer between 1 and 4, and $X^3$ represents a halogen atom, an alkoxy group having 1 to 3 carbon atoms, a vinyl group, or an ethynyl group, $R_{14}$ is $C_{1-6}$ alkyl, $C_{2-6}$ alkenyl, $C_{2-6}$-alkynyl, aryl, or heteroalkyl, and $R_{15}$ is H, $C_{1-6}$ alkyl, $C_{2-6}$ alkenyl, $C_{2-6}$-alkynyl, acyl, aryl, or heteroalkyl.

In various embodiments of the third aspect, $R_2$ is OH or $CH_3$, $R_{11}$ is a $C_{1-6}$ alkyl, $R_{15}$ is H or $CH_3$, and $R_{14}$ is $C_{1-6}$ alkyl. In particular embodiments, the compound has one of the chemical structures below:

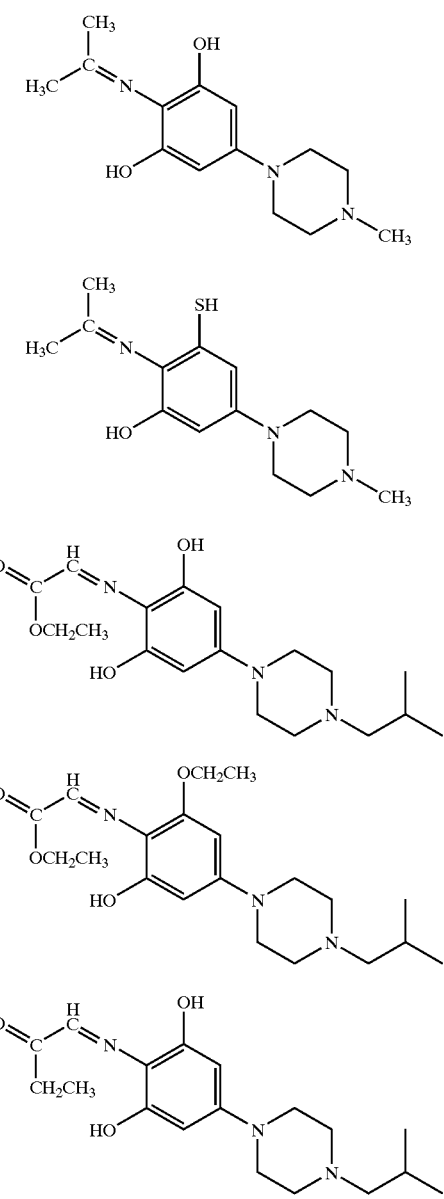

In another aspect, the invention features a method of preventing, stabilizing, or inhibiting the growth of microbes, or killing microbes. The method includes contacting microbes or a site susceptible to microbial growth with one or more compounds of formulas (I), (II), (III), (IV), or (V) in amounts sufficient to prevent, stabilize, or inhibit the growth of the microbes, or kill the microbes.

In one embodiment of the above aspect, the step of contacting microbes or a site susceptible to microbial growth with the compound includes administering to a mammal the compound in an amount sufficient to treat, stabilize, or prevent the microbial infection.

Microbial infections to be treating using compounds of formulas (I), (II), (III), (IV), or (V) include, for example, *H. pylori* associated ulcers, antibiotic associated *colitis*, sexually transmitted diseases, community acquired pneumonia, and respiratory infections.

The invention also features a method for treating a microbial infection in an animal, the method including administering to the animal (i) an antimicrobial agent and (ii) a compound having the chemical structure of formula (I), (II), (III), (IV), or (V). Accordingly, the invention features a method of treating a microbial infection in an animal comprising co-administering a compound of any of formulas (I), (II), (III), (IV), or (V) along with one or more antifungal agents, antiviral agents, antibacterial agents, or antiprotozoan agents, or combinations thereof.

In another aspect, the invention also features a method of enhancing the antimicrobial activity of an antimicrobial agent against a microbe. This method includes the step of contacting the microbe with the antimicrobial agent and a compound having the chemical structure of formula (I), (II), (III), (IV), or (V) in an amount effective to increase the antimicrobial activity of the antimicrobial agent.

The invention also features a method of treating a patient having a chronic disease associated with a bacterial infection. The method includes the step of administering to a patient a compound having the chemical structure of formula (I), (II), (III), (IV), or (V).

The chronic disease may be an inflammatory disease. Examples of inflammatory diseases include but are not limited to asthma, coronary artery disease, arthritis, conjunctivitis, lymphogranuloma venerum (LGV), cervicitis, and salpingitis. The chronic disease can also be an autoimmune disease (e.g., systemic lupus erythematosus, diabetes mellitus, graft versus host disease). In a most preferred embodiment of the invention, the chronic disease is atherosclerosis. In addition, the preferred embodiments of the invention provide for any chronic disease that occurs in an immuno-compromised patient (e.g., an individual infected with HIV or an individual undergoing chemotherapy).

In yet another aspect, the invention features a pharmaceutical composition including a compound having the chemical structure of formula (I), (II), (III), or (IV) and a pharmaceutically acceptable excipient, wherein the compound is in an amount effective to increase the antimicrobial activity of an antimicrobial agent.

In any of the foregoing aspects of the invention, suitable compounds include compounds having one of the structures shown above.

Compounds useful in the invention include those described herein in any of their pharmaceutically acceptable forms, including isomers such as diastereomers and enantiomers, salts, solvates, and polymorphs thereof, as well as racemic mixtures of the compounds described herein.

In the generic descriptions of compounds of this invention, the number of atoms of a particular type in a substituent group is generally given as a range. For example, an alkyl group containing from 1 to 4 carbon atoms is indicated as $C_{1-4}$ alkyl. Such a range reference is intended to include specific references to groups having each of the integer number of atoms within the specified range. For example, $C_1$–$C_4$ includes each of $C_1$, $C_2$, $C_3$ and $C_4$. Other numbers of atoms and other types of atoms are indicated in a similar manner.

Unless otherwise indicated, the term "alkyl" refers to a branched or unbranched aliphatic hydrocarbon group, preferably having from 1 to 6 carbon atoms, and more preferably 1 to 4 carbon atoms. Preferably the hydrocarbon group is saturated. The alkyl group may optionally be substituted, and some preferred substituents include alkoxy, alkylthio, halogen, fluoroalkyl, perfluoralkyl, amino, monosubstituted amino, disubstituted amino, hydroxyalkyl, carboxyalkyl and carboxy groups. Exemplary alkyl groups include methyl; ethyl; n-propyl; isopropyl; n-butyl; iso-butyl; sec-butyl; tert-butyl; pentyl; cyclopropyl; cyclobutyl; cyclopentyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and n-hexyl.

By "alkenyl" is meant a branched or unbranched hydrocarbon group containing one or more double bonds, desirably having from 2 to 6 carbon atoms. An alkene may optionally include monocyclic, bicyclic, or tricyclic rings, in which each ring desirably has five or six members. The alkene group may be substituted or unsubstituted. Exemplary substituents include alkoxy, aryloxy, sulfhydryl, alkylthio, arylthio, halogen, hydroxyl, fluoroalkyl, perfluoralkyl, amino, aminoalkyl, disubstituted amino, quaternary amino, hydroxyalkyl, carboxyalkyl, and carboxyl groups.

By "alkynyl" is meant a branched or unbranched hydrocarbon group containing one or more triple bonds, desirably having from 2 to 6 carbon atoms. An alkyne may optionally include monocyclic, bicyclic, or tricyclic rings, in which each ring desirably has five or six members. The alkyne group may be substituted or unsubstituted. Exemplary substituents include alkoxy, aryloxy, sulfhydryl, alkylthio, arylthio, halogen, hydroxyl, fluoroalkyl, perfluoralkyl, amino, aminoalkyl, disubstituted amino, quaternary amino, hydroxyalkyl, carboxyalkyl, and carboxyl groups.

The term "fluoroalkyl" refers to a lower alkyl group that is substituted with a fluorine. The term "perfluoroalkyl" refers to a lower alkyl group that is substituted with a fluorine atom in every available position except for where the lower alkyl group is attached to the main chain.

The term "carboxyalkyl" refers to a chemical moiety with formula —$(R)_n$—COOH, where R is an alkyl moiety, preferably a saturated alkyl, and where n is 0–5.

The term "hydroxyalkyl" refers to a chemical moiety with the formula —$(R)_n$—OH, where R is an alkyl moiety and where n is 1–4.

The term "alkoxy" refers to a chemical substituent of formula —OR, where R is hydrogen or a saturated or unsaturated lower alkyl moiety.

The term "alkylthio" refers to a chemical substituent of formula —SR, where R is hydrogen or a saturated or unsaturated lower alkyl moiety.

The term "aryl" refers to an aromatic group having at least one ring having a conjugated π electron system and includes both carbocyclic aryl (e.g., phenyl) and heterocyclic aryl groups (e.g., imidazole). The ring of the aryl group is preferably 5 to 10 atoms. The aromatic ring may be exclusively composed of carbon atoms or may be composed of a mixture of carbon atoms and heteroatoms. Preferred heteroatoms include nitrogen, oxygen, sulfur, and phosphorous. Aryl moieties include monocyclic, bicyclic, and tricyclic rings, where each ring has preferably five or six members. The aryl moiety may be optionally monosubstituted or disubstituted with lower alkyl, hydroxyl, alkoxy, alkylthio, halogen, fluoroalkyl, carboxyalkyl, amino, monosubstituted amino, and disubstituted amino.

By "heteroalkyl" is meant a branched or unbranched group in which one or more methylenes (—$CH_2$—) are replaced by nitrogen, oxygen, sulfur, carbonyl, thiocarbonyl, phosphoryl, sulfonyl, or NR, where R is an alkyl. Some examples include tertiary amines, ethers, thioethers, amides, thioamides, carbamates, thiocarbamates, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halogen, hydroxyl, fluoroalkyl, perfluoralkyl, amino, aminoalkyl, disubstituted amino, quaternary amino, hydroxyalkyl, carboxyalkyl, and carboxyl groups.

By "acyl" is meant the group —C(O)—Z, where Z is $C_{1-6}$ alkyl, $C_{2-6}$ alkenyl, $C_{2-6}$-alkynyl, aryl, or heteroalkyl.

"Halogen" or "halo" refers to F, Br, Cl, or I, but is preferably F or Br, and more preferably is F.

"Hydroxyl" or "hydroxy" refers to the group —OH.

The term "amino" means the group NRR', where R and R' may independently be alkyl or hydrogen or hydroxyl, but preferably are hydrogen. The term "monosubstituted amino" refers to an amino group in which one of R or R' is alkyl. The term "disubstituted amino" refers to an amino group in which R and R' are each independently alkyl or hydroxyl.

The term "arylalkyl" refers to a lower alkyl group substituted with an aryl group. An example of an arylalkyl group is benzyl where a methyl group is substituted with phenyl. The lower alkyl group may be optionally substituted with a lower alkyl, alkoxy, alkylthio, halogen, amino, monosubstituted amino, or disubstituted amino. The arylalkyl group may be aryl-substituted where the aryl group is optionally substituted with a lower alkyl, alkoxy, alkylthio, halogen, amino, monosubstituted amino, or disubstituted amino.

The term "microbes" includes, for example, bacteria, fungi, yeasts, and protozoa.

An "antimicrobial enhancer agent" is a compound that increases a microbe's sensitivity to an antimicrobial agent. The antimicrobial enhancer agent may have intrinsic antimicrobial (e.g., antibacterial) activity of its own, but at least a significant portion of the relevant activity is due to the enhancement of the antimicrobial agent.

In one embodiment, the antimicrobial agent that is enhanced is an antibacterial agent. Various antibacterial agents can be used in conjunction with the antimicrobial enhancer agents of the present invention. These include quinolones, tetracyclines, glycopeptides, aminoglycosides, β-lactams, rifamycins, coumermycins, macrolides, ketolides, azalides, and chloramphenicol. In particular embodiments an antibiotic of the above classes can be, for example, one of the following:

β-Lactam Antibiotics: imipenem, meropenem, biapenem, cefaclor, cefadroxil, cefamandole, cefatrizine, cefazedone, cefazolin, cefixime, cefinenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763

Macrolides: azithromycin, clarithromycin, erythromycin, oleandomycin, rokitamycin, rosaramicin, roxithromycin, and troleandomycin.

Ketolides: ABT-773, Telithromycin (HMR 3647), HMR3562, HMR3004, HMR3787, ABT-773, CP-654,743 (a C2-fluoro ketolide, A1957730, and TE802.

Quinolones: amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, PD131628, PD138312, PD140248, Q-35, AM-1155, NM394, T-3761, rufloxacin, OPC-17116, DU-6859a, and DV-7751a.

Tetracyclines: chlortetracycline, demeclocycline, doxycycline, lymecycline, methacycline, minocycline, oxytetracycline, and tetracycline.

Aminoglycosides: amikacin, arbekacin, butirosin, dibekacin, fortimicins, gentamicin, kanamycin, meomycin, netilmicin, ribostamycin, sisomicin, spectinomycin, streptomycin, tobramycin, clindamycin, and lincomycin.

Rifamycins: rifamycin SV, rifamycin O, rifabutin, rifampicin, rifampin, and rifalizil.

In the context of the response of a microbe, such as a bacterium, to an antimicrobial agent, the term "susceptibility" refers to the sensitivity of the microbe for the presence of the antimicrobial agent. To increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

As used herein, the term "treating" refers to administering a pharmaceutical composition for prophylactic and/or therapeutic purposes. The term "prophylactic treatment" refers to treating a patient who is not yet infected, but who is susceptible to, or otherwise at risk of, a particular infection. The term "therapeutic treatment" refers to administering treatment to a patient already suffering from an infection to improve the patient's condition. Thus, in preferred embodiments, treating is the administration to a mammal (either for therapeutic or prophylactic purposes) of therapeutically effective amounts of a compound of any of formulas (I), (II), (III), (IV), or (V) and an antimicrobial agent in combination (either simultaneously or serially).

By "therapeutically effective amount" or "pharmaceutically effective amount" is meant an amount of a compound of any of formulas (I), (II), (III), (IV), or (V), or amounts individually of a compound of any of formulas (I), (II), (III), (IV), or (V) and an antimicrobial agent, as disclosed for this invention, which have a therapeutic effect, which generally refers to the inhibition to some extent of the normal metabolism of microbial cells causing or contributing to a microbial infection. The doses of antimicrobial enhancer agent and antimicrobial agent that are useful in combination as a treatment are therapeutically effective amounts. Thus, as used herein, a therapeutically effective amount means those amounts of antimicrobial enhancer agent and antimicrobial agent that, when used in combination, produce the desired therapeutic effect as judged by clinical trial results and/or model animal infection studies. In particular embodiments, the antimicrobial enhancer agent and antimicrobial agent are combined in predetermined proportions and thus a therapeutically effective amount would be an amount of the combination. This amount of the antimicrobial enhancer agent and antimicrobial agent individually can be routinely determined by one of skill in the art, and will vary, depending on several factors, such as the particular microbial strain involved and the particular antimicrobial enhancer agent and antimicrobial agent used. This amount can further depend upon the patient's height, weight, sex, age and medical history. For prophylactic treatments, a therapeutically effective amount is up to an amount that would be effective if a microbial infection existed.

The term "microbial infection" refers to the invasion of the host mammal by pathogenic microbes. This includes the excessive growth of microbes that are normally present in or on the body of a mammal. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the presence of a microbial population(s) is damaging the cells or other tissue of a mammal.

The term "administration" or "administering" refers to a method of giving a dosage of an antimicrobial pharmaceutical composition to a mammal, where the method is, e.g., topical, oral, intravenous, intraperitoneal, or intramuscular. The preferred method of administration can vary depending on various factors, e.g., the components of the pharmaceutical composition, site of the potential or actual bacterial infection, microbe involved, and severity of an actual microbial infection. The term "mammal" specifically includes humans, cattle, horses, dogs, and cats, but also includes many other species.

Other features and advantages of the invention will be apparent from the following detailed description.

DETAILED DESCRIPTION OF THE INVENTION

Figure 1A:
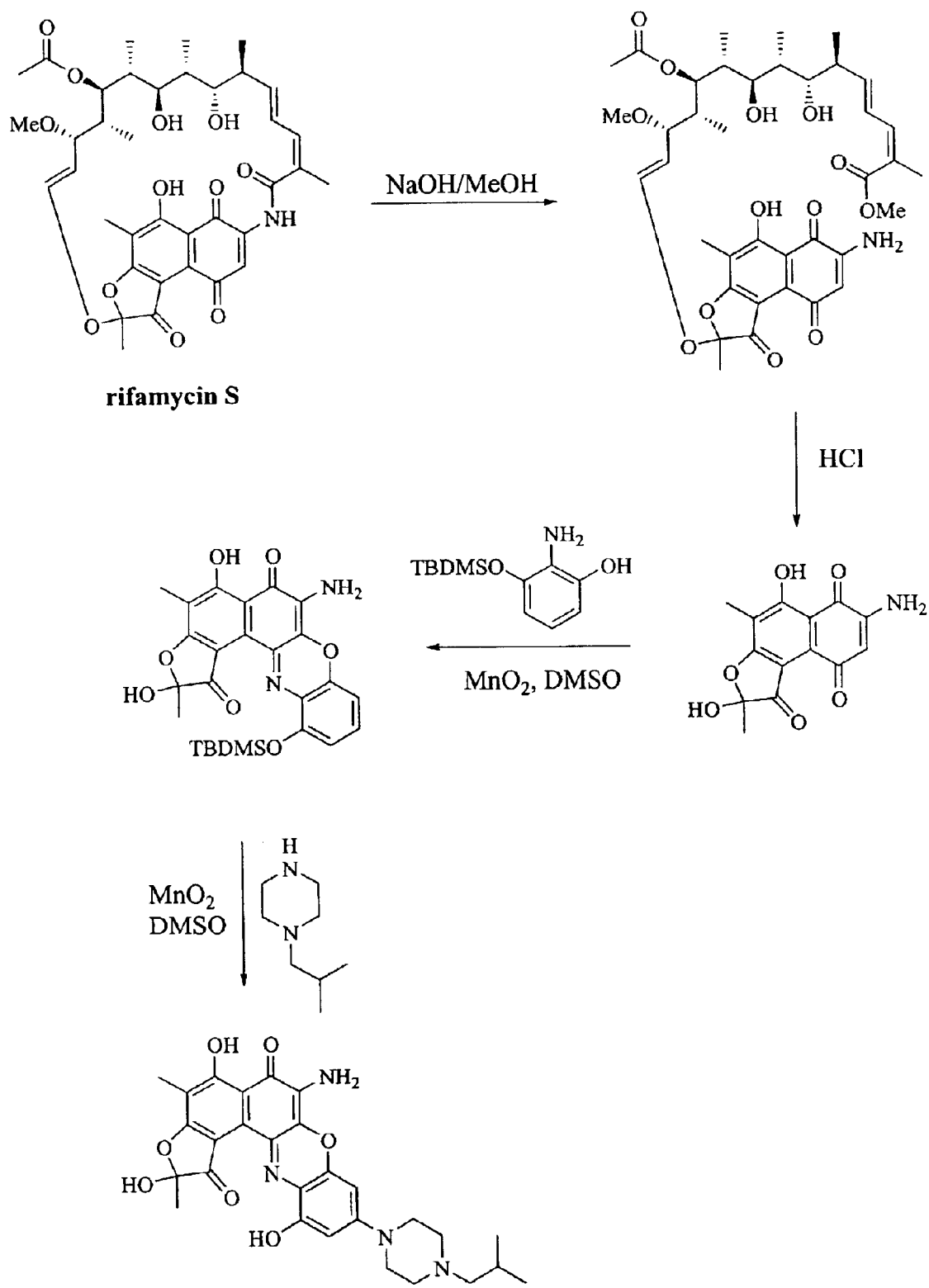
FIG. 1a is a schematic illustration depicting the steps of synthesis of compounds having the formula (I).

We have discovered a series of compounds useful as antimicrobial agents and/or antimicrobial enhancer agents. These compounds satisfy one of the formulas (I), (IV), or (V).

Antimicrobial agents and/or antimicrobial enhancer agents include compounds of formula I:

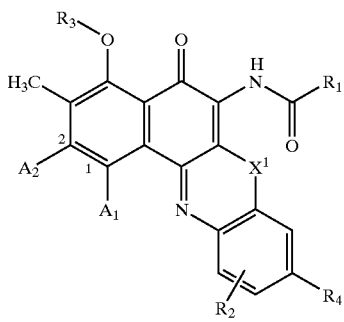

In formula I, $A_1$ and $A_2$ combine to form a fused ring described by formulas:

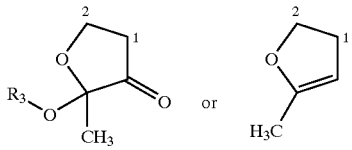

$X^1$ represents an oxygen atom or a sulfur atom, $R_1$ represents H, $C_{1-6}$ alkyl, $C_{2-6}$ alkenyl, $C_{2-6}$-alkynyl, aryl, or heteroalkyl, $R_2$ represents $OR_3$, $SR_3$, a hydrogen atom, or an alkyl group having 1 to 3 carbon atoms, each $R_3$, independently, represents H, $C_{1-6}$ alkyl, $C_{2-6}$ alkenyl, $C_{2-6}$-alkynyl, acyl, aryl, heteroalkyl, $S(O)_{1-2}$—$C_{1-6}$ alkyl, $S(O)_{1-2}$-aryl, $S(O)_{1-2}$—$C_{2-6}$ alkenyl, or $S(O)_{1-2}$—$C_{2-6}$-alkynyl, and $R_4$ represents a group expressed by the formula:

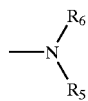

wherein each of $R_5$ and $R_6$ is, independently, an alkyl group having 1 to 7 carbon atoms, or $R_5$ and $R_6$ combine to form a 3–8 membered cyclic system, or $R_4$ represents a group expressed by the formula:

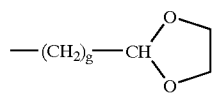

in which g represents an integer between 1 and 3;

or $R_4$ represents a group expressed by the formula:

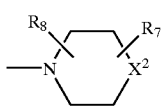

wherein each of $R_7$ and $R_8$ is, independently, a hydrogen atom or an alkyl group having 1 to 3 carbon atoms, $X^2$ represents an oxygen atom, a sulfur atom, a carbonyl group, or $X^2$ represents a group expressed by the formula:

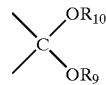

in which each of $R_9$ and $R_{10}$ is, independently, a hydrogen atom, or an alkyl group having 1 to 3 carbon atoms, or $R_9$ and $R_{10}$, in combination with each other, represent —$(CH_2)_k$— in which k represents an integer between 1 and 4;

or $X^2$ represents a group expressed by the formula:

in which m represents 0 or 1, $R_{11}$ represents a hydrogen atom, an alkyl group having 1 to 6 carbon atoms, or —$(CH_2)_nX^3$ in which n represents an integer between 1 and 4, and $X^3$ represents a halogen atom, an alkoxy group having 1 to 3 carbon atoms, a vinyl group, or an ethynyl group, or $X^2$ represents a group expressed by the formula:

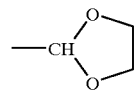

Antimicrobial agents and/or antimicrobial enhancer agents also include compounds of formula IV:

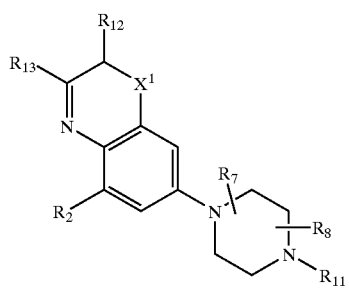

In formula IV, $X^1$ represents an oxygen atom or a sulfur atom, $R_2$ represents $OR_3$, $SR_3$, a hydrogen atom, or an alkyl group having 1 to 3 carbon atoms, each $R_3$, independently, represents H, $C_{1-6}$ alkyl, $C_{2-6}$ alkenyl, $C_{2-6}$-alkynyl, acyl, aryl, heteroalkyl, $S(O)_{1-2}$—$C_{1-6}$ alkyl, $S(O)_{1-2}$-aryl, $S(O)_{1-2}$—$C_{2-6}$ alkenyl, or $S(O)_{1-2}$—$C_{2-6}$-alkynyl, each of $R_7$ and $R_8$ is, independently, a hydrogen atom or an alkyl group having 1 to 3 carbon atoms, $R_{11}$ represents a hydrogen atom, an alkyl group having 1 to 6 carbon atoms, or —$(CH_2)_nX^3$ in which n represents an integer between 1 and 4, and $X^3$ represents a halogen atom, an alkoxy group having 1 to 3 carbon atoms, a vinyl group, or an ethynyl group; $R_{12}$ is H, O, $C_{1-6}$ alkyl, $C_{2-6}$ alkenyl, $C_{2-6}$-alkynyl, acyl, aryl, or heteroalkyl, and $R_{13}$ is H, $C_{1-6}$ alkyl, $C_{2-6}$ alkenyl, $C_{2-6}$-alkynyl, acyl, aryl, heteroalkyl, OH, SH, $OR_3$, or $SR_3$.

Antimicrobial agents and/or antimicrobial enhancer agents also include compounds of formula V:

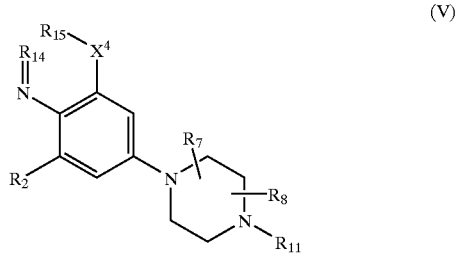

(V)

In formula V, $X^4$ represents an oxygen atom or a sulfur atom, $R_2$ represents $OR_3$, $SR_3$, a hydrogen atom, or an alkyl group having 1 to 3 carbon atoms, $R_3$ represents H, $C_{1-10}$ alkyl, $C_{2-10}$ alkenyl, $S(O)_{1-2}$—$C_{1-10}$-alkyl, $S(O)_{1-2}$—$C_{1-10}$-aryl, $S(O)_{1-2}$—$C_{1-10}$-heteroaryl, or $S(O)_{1-2}$—$C_{1-10}$-heterocyclyl, wherein each of $R_7$ and $R_8$ is, independently, a hydrogen atom or an alkyl group having 1 to 3 carbon atoms $R_{11}$ represents a hydrogen atom, an alkyl group having 1 to 6 carbon atoms, or —$(CH_2)_n X^3$ in which n represents an integer between 1 and 4, and $X^3$ represents a halogen atom, an alkoxy group having 1 to 3 carbon atoms, a vinyl group, or an ethynyl group, $R_{14}$ is $C_{1-6}$ alkyl, $C_{2-6}$ alkenyl, $C_{2-6}$-alkynyl, aryl, or heteroalkyl, and $R_{15}$ is H, $C_{1-6}$ alkyl, $C_{2-6}$ alkenyl, $C_{2-6}$-alkynyl, acyl, aryl, or heteroalkyl.

In Vivo Evaluation of Antimicrobial Enhancer Activity

Antimicrobial enhancer activity is generally initially characterized in vitro using standard assays. Those which show effective enhancement of antimicrobial agent activity can be selected for evaluation in vivo. Efficacy testing can be performed using standard procedures. For example, primary efficacy evaluation may be done using any standard in vivo bacterial infection model. Treatment is initiated, varying either or both time(s) of treatment and dose of antibiotic. In these experiments the doses of both the antimicrobial agent and the antimicrobial enhancer agent are varied. A positive result is indicated by significant increase in protection from the infection by the combination of the antimicrobial enhancer agent and the antimicrobial agent, compared to the antimicrobial agent alone.

The examples of infection models provided are not limiting. As understood by those skilled in the art, other models can be utilized as appropriate for a specific infecting microbe. In particular, cell-based infection models may be used in some circumstances instead of animal models.

Evaluation of Antimicrobial Activity

Compounds of formulas (I), (II), (III), (IV), or (V) can be assayed by using standard in vitro models or animal models to evaluate antimicrobial activity. These assays are presently described in the literature and are familiar to those skilled in the art. These include but are not limited to assays for monitoring inflammation, microbial infection, and autoimmune diseases (e.g., atherosclerosis, MS, and rheumatoid arthritis, each of which may be associated with microbial infection).

Compounds of the present invention can be screened for antimicrobial activity by measuring their minimum inhibitory concentration (MIC), using standard MIC in vitro assays (see, for example, Tomioka et al., *Antimicrob. Agents Chemother.* 37:67, 1993). Agents can be screened against *Chlamydophila pneumoniae, Chlamydia trachomatis, Mycobacterium tuberculosis* (including multiple drug resistant strains), *Mycobacterium avium* complex, and other intracellular infectious bacteria. Details of a standard MIC assay are provided in Example 7.

In addition, compounds can be evaluated using standard in vivo animal models of infection and autoimmune disease (e.g., atherosclerosis, MS, rheumatoid arthritis).

Therapy

The compounds of the present invention can be used alone or in conjunction with any antimicrobial agent, including, for example, quinolones, tetracyclines, glycopeptides, aminoglycosides, β-lactams, rifamycins, coumermycins, macrolides, ketolides, azalides, and chloramphenicol. Exemplary antimicrobial agents are provided above.

Microbial infections that can be treated or prevented include infections by bacteria, fungi, yeasts, and protozoa.

The microbial infection to be treated or prevented by one or more compounds of formulas (I), (II), (III), (IV), or (V) can be an infection by a bacterium, such as *Acinetobacter calcoaceticus, A. haemolyticus, Aeromonas hydrophilia, Bacteroides fragilis, B. distasonis, Bacteroides* 3452A homology group, *B. vulgatus, B. ovalus, B. thetaiotaomicron, B. uniformis, B. eggerthii, B. splanchnicus, Branhamella catarrhalis, Campylobacterfetus, C. jejuni, C. coli, Citrobacterfreundii, Clostridium difficile, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. macginleyi, C. matruchoti, C. mucifaciens, C. pilosum, C. propinquum, C. renale, C. riegelii, C. sanguinis, C. singulare, C. striatum, C. sundsvallense, C. thomssenii, C. urealyticum, C. xerosis, Enterobacter cloacae, E. aerogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Francisella tularensis, Gardnerella vaginalis, Helicobacter pylori, Kingella dentrificans, K. kingae, K. oralis, Klebsiella pneumoniae, K. oxytoca, Moraxella catarrhalis, M. atlantae, M. lacunata, M. nonliquefaciens, M. osloensis, M. phenylpyruvica, Morganella morganii, Parachlamydia acanthamoebae, Pasteurella multocida, P. haemolytica, Proteus mirabilis, Proteus vulgaris, Providencia alcalifaciens, P. rettgeri, P. stuartii, Serratia marcescens, Simkania negevensis, Streptococcus pneumoniae, S. agalactiae, S. pyogenes, Treponema pallidum, Vibrio cholerae,* and *V. parahaemolyticus.* Accordingly, the invention features a method of treating infections by the bacteria above, among others.

The microbial infection to be treated or prevented by one or more compounds of formulas (I), (II), (III), (IV), or (V) may be an intracellular infection by a facultative or obligate intracellular microbe.

Compounds of formulas (I), (II), (III), (IV), or (V) may be used to treat or prevent bacterial infections by facultative intracellular bacteria, such as *Bordetella pertussis, B. parapertussis, B. bronchiseptica, Burkholderia cepacia, Escherichia coli, Haemophilus actinomycetemcomitans, H. aegyptius, H. aphrophilus, H. ducreyi, H. felis, H. haemoglobinophilus, H. haemolyticus, H. influenzae, H. paragallinarum, H. parahaemolyticus, H. parainfluenzae, H. paraphrohaemolyticus, H. paraphrophilus, H. parasuis, H. piscium, H. segnis, H. somnus, H. vaginalis, Legionella adelaidensis, L. anisa, L. beliardensis, L. birminghamensis, L. bozemanii, L. brunensis, L. cherrii, L. cincinnatiensis, Legionella drozanskii L. dumoffli, L. erythra, L. fairfieldensis, L. fallonii, L. feeleii, L. geestiana, L.* gormanii, L. gratiana, L. gresilensis, L. hackeliae, L. israelensis, L. jordanis, L. lansingensis, Legionella londiniensis L. longbeachae, Legionella lytica L. maceachernii, L. micdadei, L. moravica, L. nautarum, L. oakridgensis, L. parisiensis, L. pittsburghensis, L. pneumophila, L. quateirensis, L. quinlivanii, L. rowbothamii, L. rubrilucens, L. sainthelensi, L. santicrucis, L. shakespearei, L. spiritensis, L. steigerwaltii, L. taurinensis, L. tucsonensis, L. wadsworthii, L. waltersii, L. worsleiensis, Listeria denitrificans, L. grayi, L. innocua, L. ivanovii, L. monocytogenes, L. seeligeri, L. welshimeri, Mycobacterium abscessus, M. africanum, M. agri, M. aichiense, M. alvei, M. asiaticum, M, aurum, M. austroafricanum, M. avium, M. bohemicum, M. bovis, M. branderi, M. brumae, M. celatum, M. chelonae, M. chitae, M. chlorophenolicum, M. chubuense, M. confluentis, M. conspicuum, M. cookii, M. diernhoferi, M. doricum, M. duvalii, M. elephantis, M. fallax, M. farcinogenes, M. flavescens, M. fortuitum, M. frederiksbergense, M. gadium, M. gastri, M. genavense, M. gilvum, M. goodii, M. gordonae, M. haemophilum, M. hassiacum, M. heckeshornense, M. heidelbergense, M. hiberniae, M. immunogenum, M. intracellulare, M. interjectum, M. intermedium, M. kansasii, M. komossense, M. kubicae, M. lentiflavum, M. leprae, M. lepraemurium, M. luteum, M. madagascariense, M. mageritense, M. malmoense, M. marinum, M. microti, M. moriokaense, M. mucogenicum, M. murale, M. neoaurum, M. nonchromogenicum, M. novocastrense, M. obuense, M. parqfortuitum, M. paratuberculosis, M. peregrinum, M. phage, M. phlei, M. porcinum, M. poriferae, M. pulveris, M. rhodesiae, M. scrofulaceum, M. senegalense, M. septicum, M. shimoidei, M. simiae, M. smegmatis, M. sphagni, M. szulgai, M. terrae, M. thermoresistibile, M. tokaiense, M. triplex, M. triviale, M. tuberculosis, M. tusciae, M. ulcerans, M. vaccae, M. wolinskyi, M. xenopi, Neisseria animalis, N. canis, N. cinerea, N. denitrificans, N. dentiae, N. elongata, N. flava, N. flavescens, N. gonorrhoeae, N. iguanae, N. lactamica, N. macacae, N. meningitidis, N. mucosa, N. ovis, N. perflava, N. pharyngis var. flava, N. polysaccharea, N. sicca, N. subflava, N. weaveri, Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Salmonella bacteriophage, S. bongori, S. choleraesuis, S. enterica, S. enteritidis, S. paratyphi, S. typhi, S. typhimurium, S. typhimurium, S. typhimurium, S. typhimurium bacteriophage, Shigella boydii, S. dysenteriae, S. flexneri, S. sonnei, Staphylococcus arlettae, S. aureus, S. auricularis, S. bacteriophage, S. capitis, S. caprae, S. carnosus, S. caseolyticus, S. chromogenes, S. cohnii, S. delphini, S. epidermidis, S. equorum, S. felis, S. fleurettii, S. gallinarum, S. haemolyticus, S. hominis, S. hyicus, S. intermedius, S. kloosii, S. lentus, S. lugdunensis, S. lutrae, S. muscae, S. mutans, S. pasteuri, S. phage, S. piscifermentans, S. pulvereri, S. saccharolyticus, S. saprophyticus, S. schleiferi, S. sciuri, S. simulans, S. succinus, S. vitulinus, S. warneri, S. xylosus, Ureaplasma urealyticum, Yersinia aldovae, Y. bercovieri, Y. enterocolitica, Y. frederiksenii, Y. intermedia, Y. kristensenii, Y. mollaretii, Y. pestis, Y. philomiragia, Y. pseudotuberculosis, Y. rohdei, and Y. ruckeri.

Compounds of formulas (I), (II), (III), (IV), or (V) may also be used to treat or prevent bacterial infections by obligate intracellular bacteria, such as Anaplasma bovis, A. caudatum, A. centrale, A. marginale A. ovis, A. phagocytophila, A. platys, Bartonella bacilliformis, B. clarridgeiae, B. elizabethae, B. henselae, B. henselae phage, B. quintana, B. taylorii, B. vinsonii, Borrelia afzelii, B. andersonii, B. anserina, B. bissettii, B. burgdorferi, B. crocidurae, B. garinii, B. hermsii, B. japonica, B. miyamotoi, B. parkeri, B. recurrentis, B. turdi, B. turicatae, B. valaisiana, Brucella abortus, B. melitensis, Chlamydia pneumoniae, C. psittaci, C. trachomatis, Cowdria ruminantium, Coxiella burnetii, Ehrlichia canis, E. chaffeensis, E. equi, E. ewingii, E. muris, E. phagocytophila, E. platys, E. risticii, E. ruminantium, E. sennetsu, Haemobartonella canis, H. felis, H. muris, Mycoplasma arthriditis, M. buccale, M. faucium, M. fermentans, M. genitalium, M. hominis, M. laidlawii, M. lipophilum, M. orale, M. penetrans, M. pirum, M. pneumoniae, M. salivarium, M. spermatophilum, Rickettsia australis, R. conorii, R. felis, R. helvetica, R. japonica, R. massiliae, R. montanensis, R. peacockii, R. prowazekii, R. rhipicephali, R. rickettsii, R. sibirica, and R. typhi. Accordingly, the invention features a method of treating infections caused by the obligate and facultative intracellular bacteria above, among others.

Compounds of formulas (I), (II), (III), (IV), or (V) may be used to treat or prevent fungal infections by a facultative intracellular fungi, such as Candida Candida aaseri, C. acidothermophilum, C. acutus, C. albicans, C. anatomiae, C. apis, C. apis var. galacta, C. atlantica, C. atmospherica, C. auringiensis, C. bertae, C. berthtae var. chiloensis, C. berthetii, C. blankii, C. boidinii, C. boleticola, C. bombi, C. bombicola, C. buinensis, C. butyri, C. cacaoi, C. cantarellii, C. cariosilignicola, C. castellii, C. castrensis, C. catenulata, C. chilensis, C. chiropterorum, C. coipomensis, C. dendronema, C. deserticola, C. diddensiae, C. diversa, C. entomaea, C. entomophila, C. ergatensis, C. ernobii, C. ethanolica, C. ethanothermophilum, C. famata, C. fluviotilis, C. fragariorum, C. fragicola, C. friedrichii, C. fructus, C. geochares, C. glabrata, C. glaebosa, C. gropengiesseri, C. guilliermondii, C. guilliermondii var. galactosa, C. guilliermondii var. soya, C. haemulonii, C. halophila/C. versatilis, C. holmii, C. humilis, C. hydrocarbofumarica, C. inconspicua, C. insectalens, C. insectamans, C. intermedia, C. javanica, C. kefyr, C. krissii, C. krusei, C. krusoides, C. lambica, C. lusitaniae, C. magnoliae, C. maltosa, C. mamillae, C. maris, C. maritima, C. melibiosica, C. melinii, C. methylica, C. milleri, C. mogii, C. molischiana, C. montana, C. multis-gemmis, C. musae, C. naeodendra, C. nemodendra, C. nitratophila, C. norvegensis, C. norvegica, C. oleophila, C. oregonensis, C. osornensis, C. paludigena, C. parapsilosis, C. pararugosa, C. periphelosum, C. petrohuensis, C. petrophilum, C. philyla, C. pignaliae, C. pintolopesii var. pintolopesii, C. pintolopesii var. slooffiae, C. pinus, C. polymorpha, C. populi, C. pseudointermedia, C. quercitrasa, C. railenensis, C. rhagii, C. rugopelliculosa, C. rugosa, C. sake, C. salmanticensis, C. savonica, C. sequanensis, C. shehatae, C. silvae, C. silvicultrix, C. solani, C. sonorensis, C. sorbophila, C. spandovensis, C. sphaerica, C. stellata, C. succiphila, C. tenuis, C. terebra, C. tropicalis, C. utilis, C. valida, C. vanderwaltii, C. vartiovaarai, C. veronae, C. vini, C. wickerhamii, C. xestobii, C. zeylanoides, and Histoplasma capsulatum. Accordingly, the invention features a method of treating an infection by the facultative intracellular fungi above, among others.

Obligate intracellular protozoans can also be treated by a compound of any of formulas (I), (II), (III), (IV), or (V). Obligate intracellular protozoans include, for example, Brachiola vesicularum, B. connori, Encephalitozoon cuniculi, E. hellem, E. intestinalis, Enterocytozoon bieneusi, Leishmania aethiopica, L. amazonensis, L. braziliensis, L. chagasi, L. donovani, L. donovani chagasi, L. donovani donovani, L. donovani infantum, L. enriettii, L. guyanensis,

*L. infantum, L. major, L. mexicana, L. panamensis, L. peruviana, L. pifanoi, L. tarentolae, L. tropica, Microsporidium ceylonensis, M. africanum, Nosema connori, N. ocularum, N. algerae, Plasmodium berghei, P. brasilianum, P. chabaudi, P. chabaudi adami, P. chabaudi chabaudi, P. cynomolgi, P. falciparum, P. fragile, P. gallinaceum, P. knowlesi, P. lophurae, P. malariae, P. ovale, P. reichenowi, P. simiovale, P. simium, P. vinckeipetteri, P. vinckei vinckei, P. vivax, P. yoelii, P. yoelii nigeriensis, P. yoelii yoelii, Pleistophora anguillarum, P. hippoglossoideos, P. mirandellae, P. ovariae, P. typicalis, Septata intestinalis, Toxoplasma gondii, Trachipleistophora hominis, T. anthropophthera, Vittaforma corneae, Trypanosoma avium, T. brucei, T. brucei brucei, T. brucei gambiense, T. brucei rhodesiense, T. cobitis, T. congolense, T. cruzi, T cyclops, T. equiperdum, T. evansi, T. dionisii, T. godfreyi, T. grayi, T. lewisi, T. mega, T. microti, T. pestanai, T. rangeli, T. rotatorium, T. simiae, T. theileri, T. varani, T. vespertilionis,* and *T. vivax.* Accordingly, the invention features a method of treating infections by the obligate intracellular protozoa above, among others.

Combination therapy according to the invention may be performed alone or in conjunction with another therapy and may be provided at home, the doctor's office, a clinic, a hospital's outpatient department, or a hospital. Treatment generally begins at a hospital so that the doctor can observe the therapy's effects closely and make any adjustments that are needed. The duration of the combination therapy depends on the type of microbial infection being treated, the age and condition of the patient, the stage and type of the patient's disease, and how the patient responds to the treatment. Additionally, a person having a greater risk of developing a microbial infection may receive prophylactic treatment to inhibit or delay an infection.

The dosage, frequency, and mode of administration of each component of the combination can be controlled independently. For example, one compound may be administered orally three times per day, while the second compound may be administered intramuscularly once per day. Combination therapy may be given in on-and-off cycles that include rest periods so that the patient's body has a chance to build healthy new cells and regain strength. The compounds may also be formulated together such that one administration delivers both compounds.

Formulation of Pharmaceutical Compositions

Compounds of formulas (I), (II), (III), (IV), or (V) can be provided alone or as a component of a pharmaceutical pack. For example, when used as an antimicrobial enhancer agent, a compound of any of formulas (I), (II), (III), (IV), or (V) and an antimicrobial agent can be formulated together or separately and in individual dosage amounts.

Administration of compounds of formulas (I), (II), (III), (IV), or (V) may be by any suitable means that results in either 1) a concentration that is an effective antimicrobial alone, or 2) a concentration of compound that increases the antimicrobial activity a antimicrobial agent administered therewith. Compounds of formulas (I), (II), (III), (IV), or (V) are admixed with a suitable carrier substance, and are generally present in an amount of 1–95% by weight of the total weight of the composition. The composition may be provided in a dosage form that is suitable for oral, parenteral (e.g., intravenous, intramuscular, subcutaneous), rectal, transdermal or topical, nasal, vaginal, inhalant, or ocular administration. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols. The efflux pump inhibitor-contaning pharmaceutical composition may be formulated according to conventional pharmaceutical practice (see, e.g., Remington: The Science and Practice of Pharmacy, (20th ed.) ed. A. R. Gennaro, 2000, Lippincott Williams & Wilkins; and Encyclopedia of Pharmaceutical Technology, eds. J. Swarbrick and J. C. Boylan, 1988–1999, Marcel Dekker, New York).

Pharmaceutical compositions according to the invention may be formulated to release the compound substantially immediately upon administration or at any predetermined time period after administration, using controlled release formulations.

Administration of compounds in controlled release formulations is useful where the compound, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

When used as an antimicrobial enhancer agent, the compound of formula (I), (II), (III), (IV), or (V) and an antimicrobial agent may be mixed together in a tablet or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Dosages

The dosage of the compound of formula (I), (II), (III), (IV), or (V) administered depends on several factors, including: whether the compound is being used as an antimicrobial agent or an antimicrobial enhancer agent, the administration method, the disease to be treated, the severity of the disease, whether the disease is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect dosage used.

As described above, the compound in question may be administered orally in the form of tablets, capsules, elixirs or syrups, or rectally in the form of suppositories. Parenteral administration of a compound is suitably performed, for example, in the form of saline solutions or with the compound incorporated into liposomes. In cases where the compound in itself is not sufficiently soluble to be dissolved, a solubilizer such as ethanol can be applied.

Synthesis

Compounds of the present invention can be synthesized using the methods described in the examples. Those skilled in the art will understand how to synthesize additional compounds within the scope of this invention based on the described syntheses and the knowledge of those skilled in the art of chemical synthesis.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Preparation of Compounds Having a 12-hydroxy-12-methylfuranone Ring

The ansa ring of Rifamycin S can be cleaved at the amide group using basic conditions as described in, for example, Bartolucci et al., *Farmaco* 50(9):587–593, 1995. Following amide cleavage, the ansa ring can be removed by cleavage at the dihydrofuranone group with boron triflouride, as described by Bartolucci, ibid (see FIG. 1a). The resulting product, compound X, is a useful starting material for the synthesis of compounds of formulas (I) and (II).

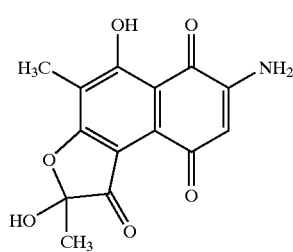

X

EXAMPLE 2

Preparation of Compounds Having a Methyl-furan Ring

Following amide cleavage, the ansa ring of rifamycin S can also be cleaved at the the dihydrofuranone group using NaBH$_4$, as described by Bartolucci, ibid. The resulting product, compound XI, a reduced form of compound X, is a useful starting material for the synthesis of compounds of formulas (I) and (III).

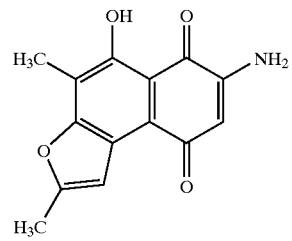

XI

EXAMPLE 3

Preparation of Compounds or Formulas (I), (II), and (III)

The compounds described by formulas (II) or (III) can be synthesized using methods analogous to those disclosed in Yamane et al., U.S. Pat. No. 4,690,919; Yamane et al., U.S. Pat. No. 4,983,602; Yamashita et al., U.S. Pat. No. 5,786,349; Yamashita et al., U.S. Pat. No. 5,981,522; Kano et al., U.S. Pat. No. 4,859,661 and *Chem. Pharm. Bull.*, 41:148, 1993, each of which is hereby incorporated by reference.

The reaction conditions previously disclosed can be used where compound X or XI is substituted for rifamycin S (see FIG. 1a).

EXAMPLE 4

Preparation of Compounds of Formula (II) Starting with the Rifamycin Derivative

Figure 1B:
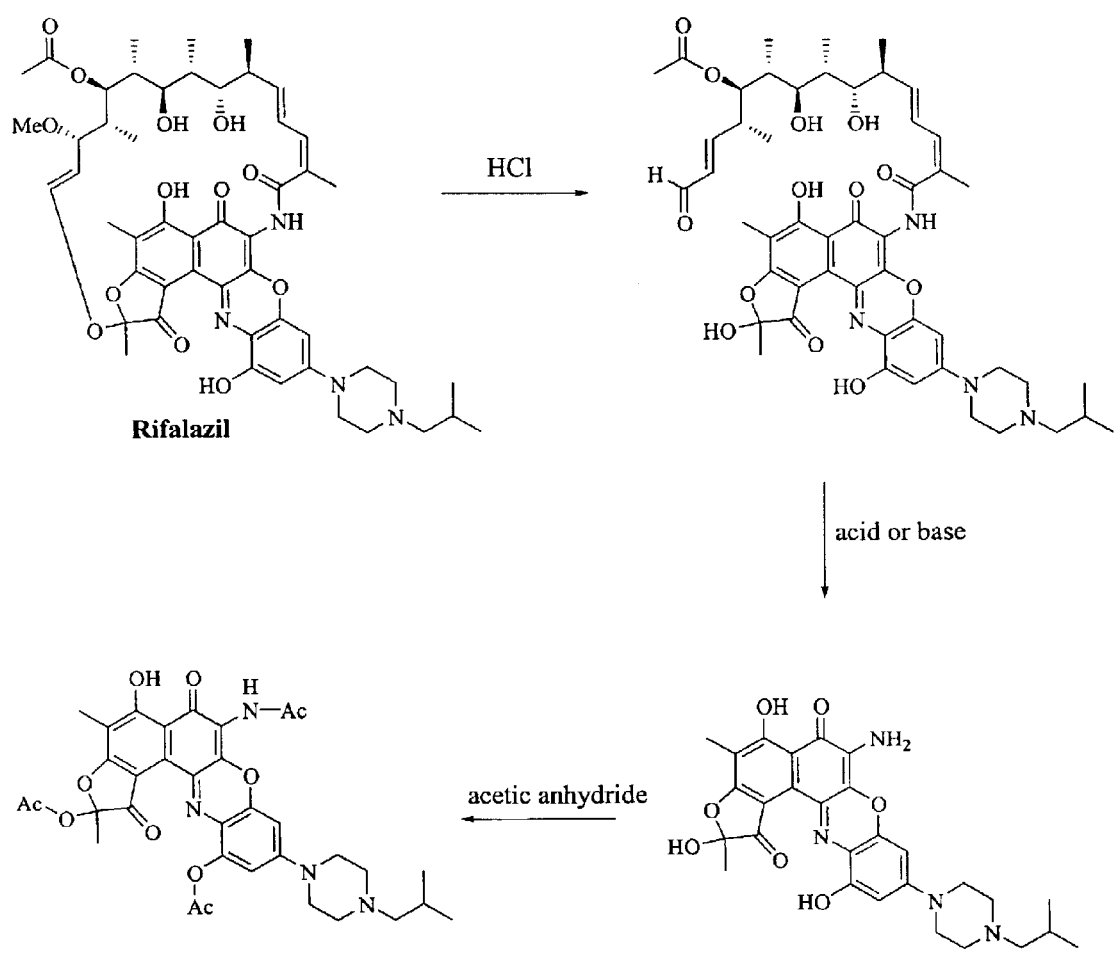
FIG. 1b is a schematic illustration depicting the steps of synthesis of compounds having the formula (I).

Alternatively, compounds of formula (II) can be prepared by starting from the rifamycin derivatives disclosed in, for example, Yamane et al., U.S. Pat. No. 4,690,919; Yamane et al., U.S. Pat. No. 4,983,602; Yamashita et al., U.S. Pat. No. 5,786,349; Yamashita et al., U.S. Pat. No. 5,981,522; Kano et al., U.S. Pat. No. 4,859,661 and *Chem. Pharm. Bull.*, 41:148, 1993, each of which is hereby incorporated by reference. The ansa ring in these compounds can be cleaved using the methods of Bartolucci, ibid. (see FIG. 1b), resulting compounds of formula (II).

EXAMPLE 5

Preparation of Compounds of Formula (V)

Figure 3:
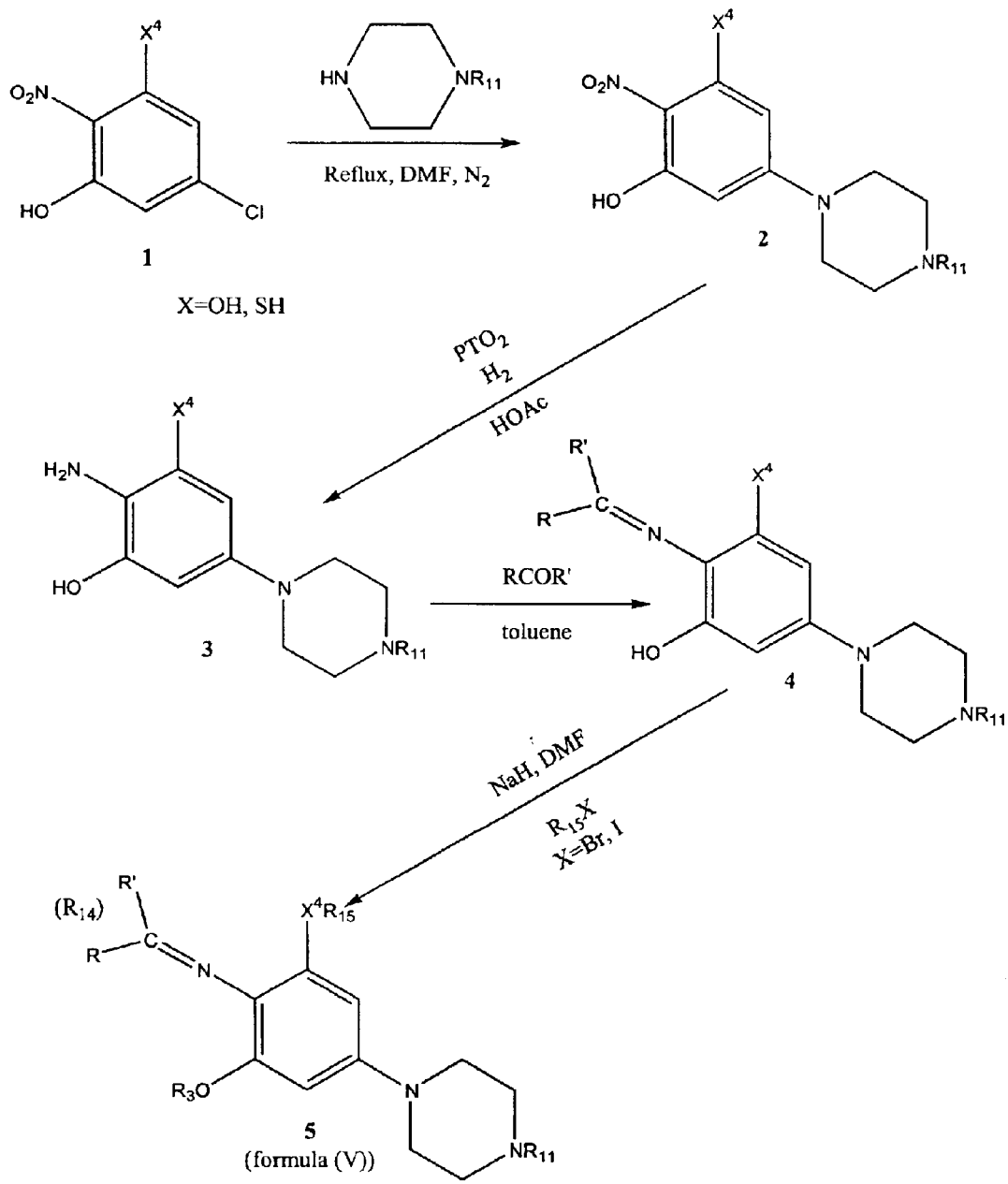
FIG. 3 is a schematic illustration depicting the steps of synthesis of compounds having the formula (V).

As shown in FIG. 3, the starting material, Compound 1, is converted into Compound 3 in two steps. A p-chloronitrobenzene with an —OH or —OR and an —SH or OH adjacent to the nitro group is employed. The —Cl is replaced by piperazine or a N-substituted piperazine to produce Compound 2, which is then reduced to the amino compound, Compound 3 (FIG. 3).

FIG. 3 also depicts the preparation of compounds satisfying formula (V). In this synthesis, Compound 3 is first condensed with a ketone or aldehyde to produce Compound 4. Compound 4 can have either a free or substituted —OH, depending on the structure of the starting material (Compound 4). When both the —OH and —X are unsubstituted, Compound 4 may be treated with alkylating agents, yielding Compound 5, which satisfies formula (V) (FIG. 3).

EXAMPLE 6

Preparation of Compounds of Formula (IV)

Figure 2:
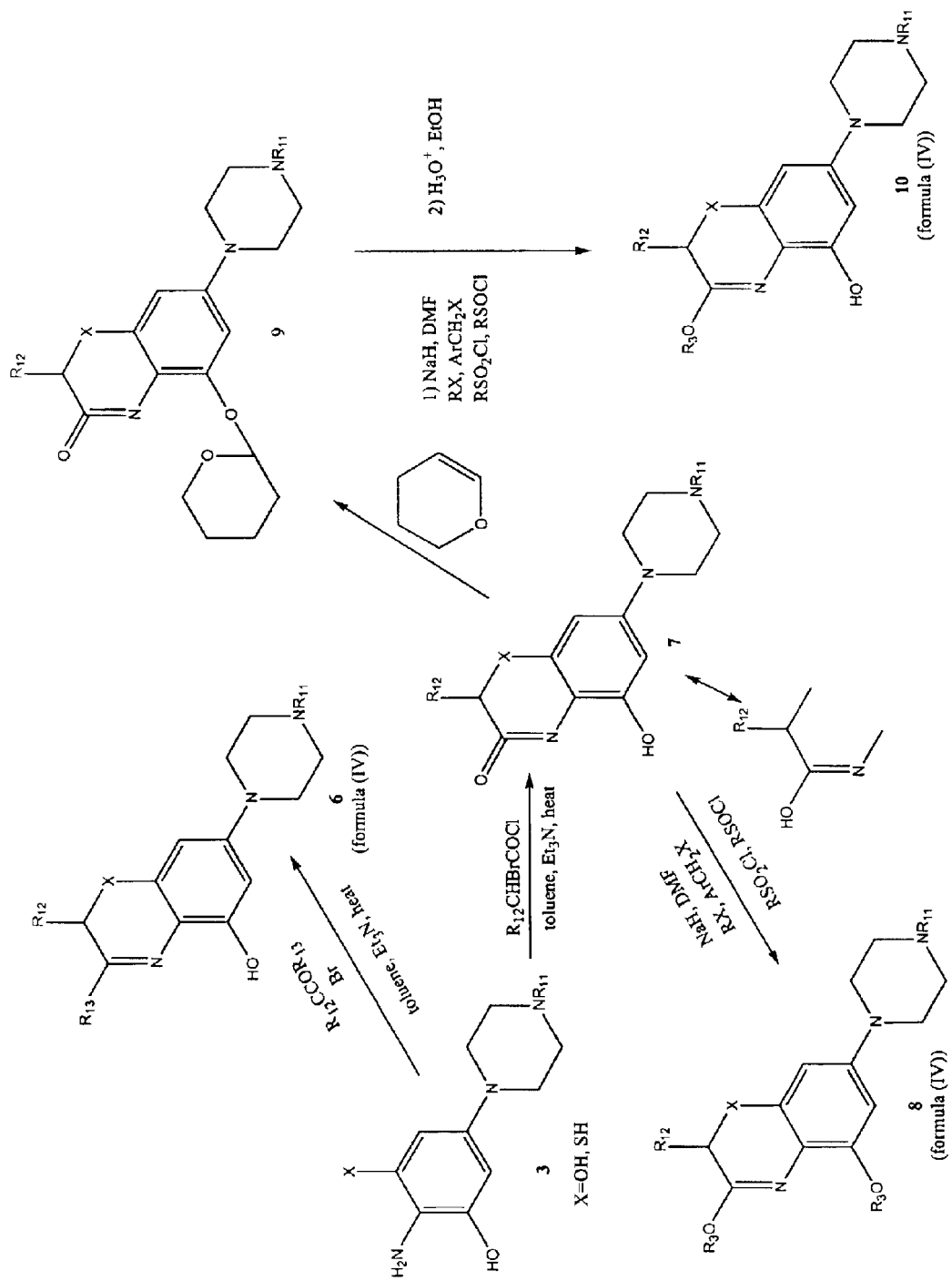
FIG. 2 is a schematic illustration depicting the steps of synthesis of compounds having the formula (IV).

As shown in FIG. 2 illustrates methods for the synthesis of compounds satisfying formula (IV). Ring closure is effected on Compound 3 with an alpha bromo ketone to produce Compound 6, which satisfies formula (IV). Alternatively, condensation of Compound 3 with an alpha bromo acyl chloride produces Compound 7. Compound 7 may then be treated with alkylating agents and RSOCl and RSO$_2$Cl to produce Compound 8, which also satisfies formula (IV).

If desired, the hydroxyl group on Compound 7 may be protected. The resulting compound, Compound 9, may be treated with alkylating agents, RSOCl, and RSO$_2$Cl, followed by removal of the protective group. This results in the synthesis of Compound 10, which also satisfies formula (IV).

EXAMPLE 7

MIC Assay

MICs of compounds of formulas (I), (II), (III), (IV), or (V) are determined by the broth microdilution method. Stock solutions of compounds were diluted in Cation Adjusted Mueller-Hinton (CAMH) broth (contains 20–25 mg of Ca$^{2+}$/L and 10–12.5 mg of Mg$^{2+}$/L) to create working solutions that were 4× the maximum concentration to be tested on each microtiter plate. The 4× working solutions were added to the wells of the 96 well microtiter plate and serially diluted two-fold across 11 wells into CAMH for *Staphylococcus aureus* and Hemophilus Test Medium (HTM) for *Hemophilus influenzae*. To prepare the test strain inoculum, 3–5 colonies of the selected bacterial strain from a pure 18–24 hour culture grown on a primary agar plate was emulsified into deionized water for *Staphylococcus aureus* and CAMH broth for *Hemophilus influenzae*, and adjusted to a 0.5 McFarland turbidity standard using a calibrated nephelometer. This suspension was then diluted further (1:100) into CAMH broth for *Staphylococcus aureus* and HTM for *Hemophilus influenzae* to yield an inoculum suspension containing approximately 10$^6$ CFU/ml. Aliquots of the inoculum suspensions were added to the compound containing wells to yield a final concentration in the well of 5×10$^5$ CFU/ml. The microtiter plates were incubated at 35–37° C. for 20–24 hours. The MIC was read as the lowest concentration of the compound that inhibits visible growth.

OTHER EMBODIMENTS

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the field of antimicrobial agents or related fields are intended to be within the scope of the invention.

What is claimed is:

1. A compound of formula I:

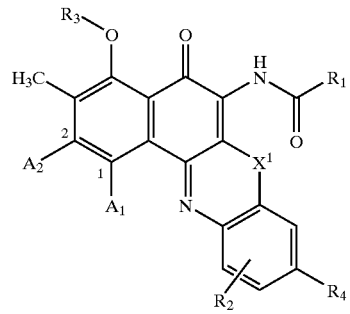

wherein A$_1$ and A$_2$ combine to form a fused ring described by formulas:

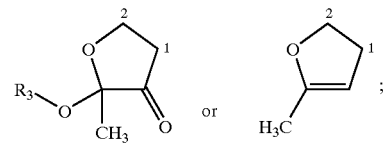

X$^1$ represents an oxygen atom.

R$_1$ represents H, C$_{1-6}$ alkyl, C$_{2-6}$ alkenyl, C$_{2-6}$-alkynyl, aryl, or heteroalkyl;

R$_2$ represents OR$_3$, SR$_3$, a hydrogen atom, or an alkyl group having 1 to 3 carbon atoms;

each R$_3$, independently, represents H, C$_{1-6}$ alkyl, C$_{2-6}$ alkenyl, C$_{2-6}$-alkynyl, acyl, aryl, heteroalkyl, S(O)$_{1-2}$—C$_{1-6}$ alkyl, S(O)$_{1-2}$-aryl, S(O)$_{1-2}$—C$_{2-6}$ alkenyl, or S(O)$_{1-2}$—C$_{2-6}$-alkynyl;

and R$_4$ represents a group expressed by the formula:

wherein each of R$_5$ and R$_6$ is, independently, an alkyl group having 1 to 7 carbon atoms, or R$_4$ represents a group expressed by the formula:

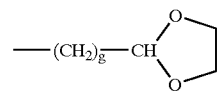

in which g represents an integer between 1 and 3; or R$_4$ represents a group expressed by the formula:

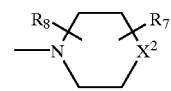

wherein each of R$_7$ and R$_8$ is, independently, a hydrogen atom or an alkyl group having 1 to 3 carbon atoms, and X$^2$ represents an oxygen atom, a sulfur atom, a carbonyl group, or X² represents a group expressed by the formula:

$$\diagdown_C\diagup^{OR_{10}}_{OR_9}$$

in which each of $R_9$ and $R_{10}$ is, independently, a hydrogen atom, or an alkyl group having 1 to 3 carbon atoms, or $R_9$ and $R_{10}$, in combination with each other, represent —(CH$_2$)$_k$— in which k represents an integer between 1 and 4;

or X² represents a group expressed by the formula:

$$\diagdown\underset{NR_{11}}{\overset{(O)_m}{|}}\diagup$$

in which m represents 0 or 1, $R_{11}$ represents a hydrogen atom, an alkyl group having 1 to 6 carbon atoms, or —(CH$_2$)$_n$X³ in which n represents an integer between 1 and 4, and X³ represents a halogen atom, an alkoxy group having 1 to 3 carbon atoms, a vinyl group, or an ethynyl group, or X² represents a group expressed by the formula:

$$-CH\diagup^{O}_{O}\diagdown$$

2. The compound of claim 1, wherein said compound is of formula II:

[Structure II]

wherein $R_1$ represents H, $C_{1-6}$ alkyl, $C_{2-6}$ alkenyl, $C_{2-6}$-alkynyl, aryl, or heteroalkyl;

$R_2$ represents OR$_3$, SR$_3$, a hydrogen atom, or an alkyl group having 1 to 3 carbon atoms;

Each $R_3$, independently, represents $C_{1-6}$ alkyl, $C_{2-6}$ alkenyl, $C_{2-6}$-alkynyl, acyl, aryl, heteroalkyl, S(O)$_{1-2}$—C$_{1-6}$ alkyl, S(O)$_{1-2}$-aryl, S(O)$_{1-2}$—C$_{2-6}$ alkenyl, or S(O)$_{1-2}$—C$_{2-6}$-alkynyl;

each of $R_7$ and $R_8$ is, independently, a hydrogen atom or an alkyl group having 1 to 3 carbon atoms;

X¹ represents an oxygen atom;

and X² represents a group expressed by the formula:

$$\diagdown\underset{NR_{11}}{\overset{(O)_m}{|}}\diagup$$

in which m represents 0 or 1, and $R_{11}$ represents a hydrogen atom, an alkyl group having 1 to 6 carbon atoms, or —(CH$_2$)$_n$X³ in which n represents an integer between 1 and 4, and X³ represents a halogen atom, an alkoxy group having 1 to 3 carbon atoms, a vinyl group, or an ethynyl group.

3. The compound of claim 1, wherein said compound is of formula III:

[Structure III]

wherein $R_1$ represents H, $C_{1-6}$ alkyl, $C_{2-6}$ alkenyl, $C_{2-6}$-alkynyl, aryl, or heteroalkyl;

$R_2$ represents OR$_3$, SR$_3$, a hydrogen atom, or an alkyl group having 1 to 3 carbon atoms;

each $R_3$, independently, represents $C_{1-6}$ alkyl, $C_{2-6}$ alkenyl, $C_{2-6}$-alkynyl, acyl, aryl, heteroalkyl, S(O)$_{1-2}$—C$_{1-6}$ alkyl, S(O)$_{1-2}$-aryl, S(O)$_{1-2}$—C$_{2-6}$ alkenyl, or S(O)$_{1-2}$—C$_{2-6}$-alkynyl;

each of $R_7$ and $R_8$ is, independently, a hydrogen atom or an alkyl group having 1 to 3 carbon atoms;

X¹ represents an oxygen atom;

and X² represents a group expressed by the formula:

$$\diagdown\underset{NR_{11}}{\overset{(O)_m}{|}}\diagup$$

in which m represents 0 or 1, and $R_{11}$ represents a hydrogen atom, an alkyl group having 1 to 6 carbon atoms, or —(CH$_2$)$_n$X³ in which n represents an integer between 1 and 4, and X³ represents a halogen atom, an alkoxy group having 1 to 3 carbon atoms, a vinyl group, or an ethynyl group.

4. A method of treating an infection of microbes selected from bacteria, fungi, and protozoans, or killing said microbes, said method comprising contacting said microbe or a site susceptible to microbial growth with a compound of claim 1 in an amount sufficient to treat said infection.

5. The method of claim 4, wherein contacting said microbes comprises administering said compound to a mammal in an amount effective to treat a microbial infection.

6. The method of claim 5, wherein said compound of claim 1 is administered in parallel with one or more antifungal agents, antibacterial agents, or antiprotozoan agents, or combinations thereof.

7. A method of enhancing the antimicrobial activity of an antimicrobial agent against a microbe, said method comprising:
   a. contacting the microbe with the antimicrobial agent; and
   b. contacting the microbe with a compound of claim 1 in an amount effective to increase the antimicrobial activity of the antimicrobial agent.

8. A method of treating disease associated with a bacterial infection in a patient, said method comprising administering to said patient a compound of claim 1 in amounts sufficient to treat said disease.

9. The method of claim 8, wherein said disease in an inflammatory disease.

10. A pharmaceutical composition comprising an effective amount of a compound of claim 1, or a suitable salt thereof, together with a pharmaceutically acceptable carrier or diluent.

11. The compound of claim 1, wherein said compound has the structure:

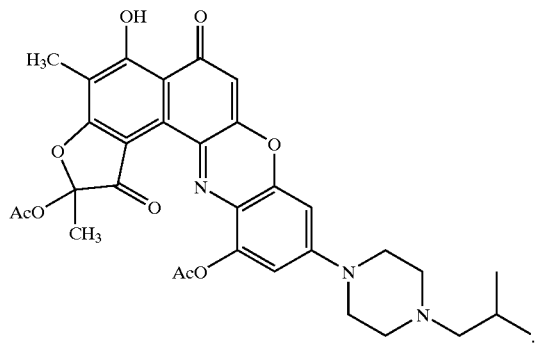

12. The compound of claim 1, wherein said compound has the structure:

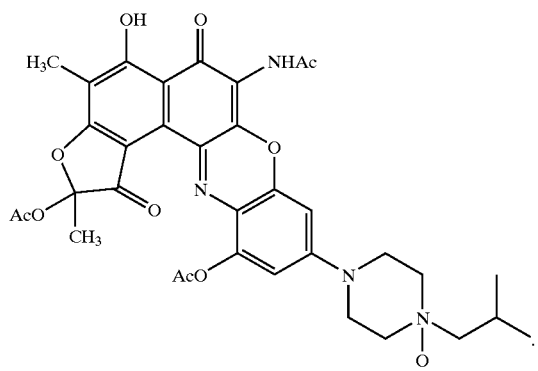

13. The compound of claim 1, wherein said compound has the structure:

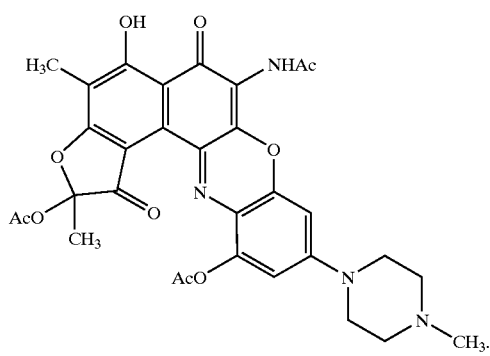

14. The compound of claim 1, wherein said compound has the structure:

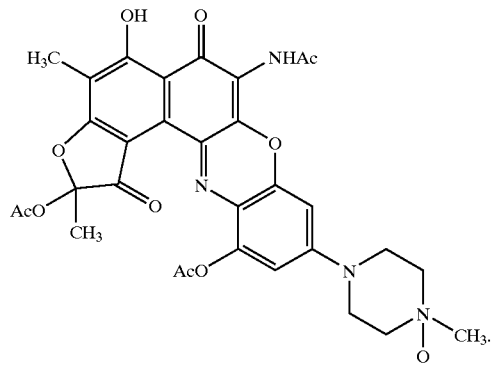

15. The compound of claim 1, wherein said compound has the structure:

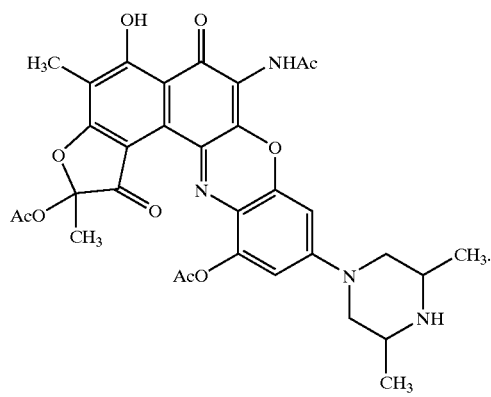

16. The compound of claim 1, wherein said compound has the structure:

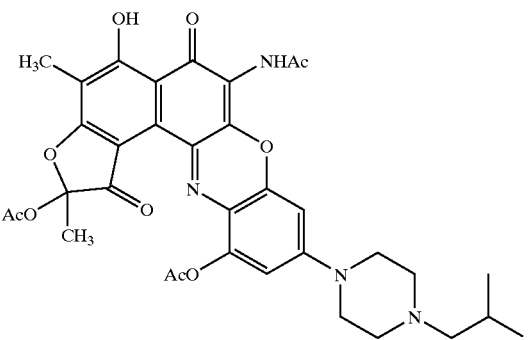

17. The compound of claim 1, wherein said compound has the structure:

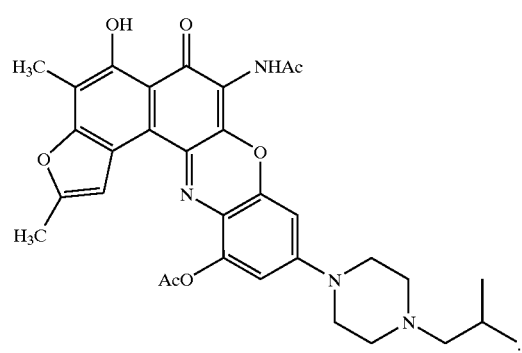

18. The compound of claim 1, wherein said compound has the structure:

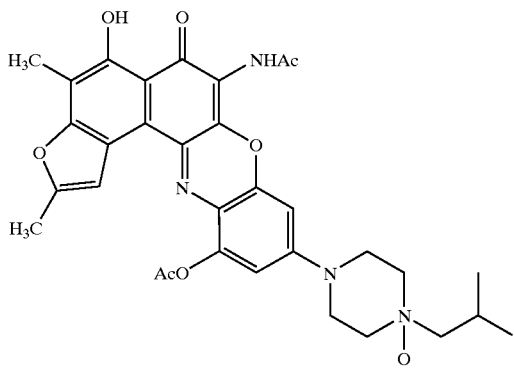

19. The compound of claim 1, wherein said compound has the structure:

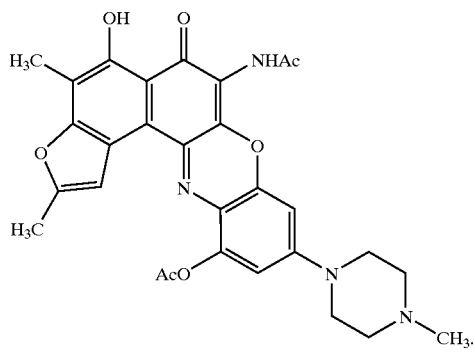

20. The compound of claim 1, wherein said compound has the structure:

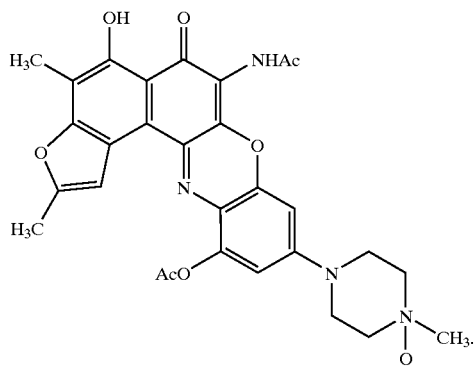

21. The compound of claim 1, wherein said compound has the structure:

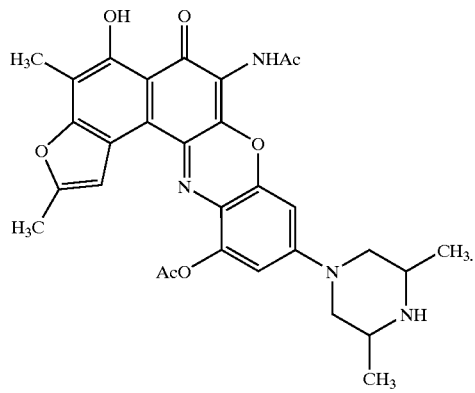

22. The compound of claim 1, wherein said compound has the structure:

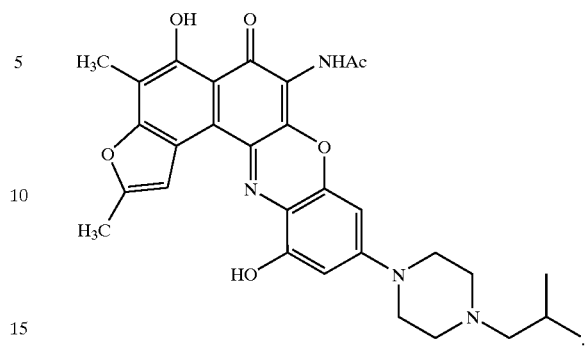

23. The method of claim 4, wherein said infection of microbes is an infection of bacteria.

24. The method of claim 23, wherein said compound the structure:

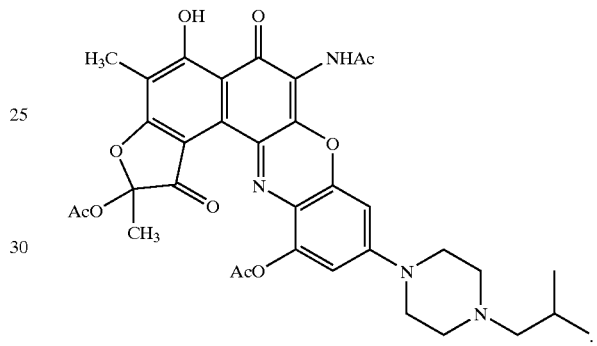

25. The method of claim 23, wherein said compound has the structure:

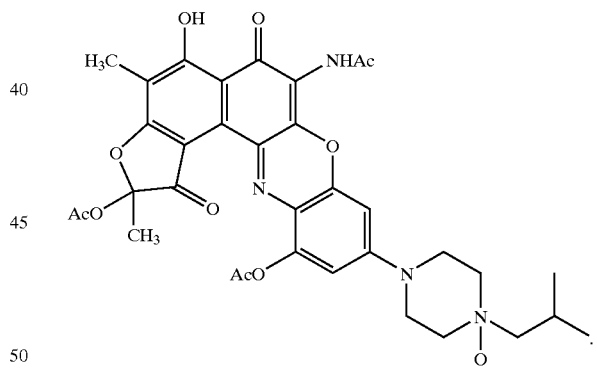

26. The method of claim 23, wherein said compound has the structure:

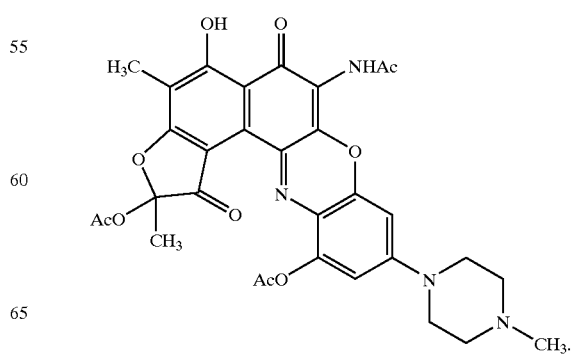

27. The method of claim 23, wherein said compound has the structure:

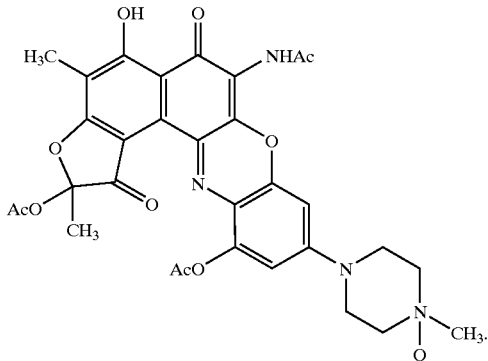

28. The method of claim 23, wherein said compound has the structure:

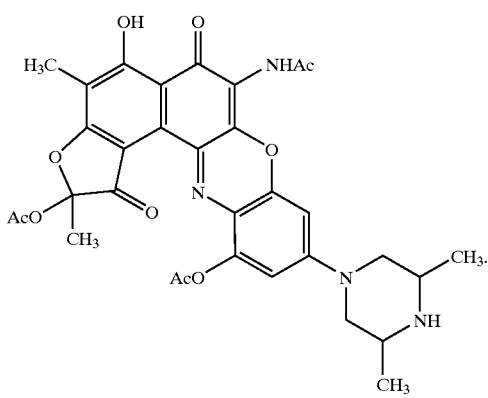

29. The method of claim 23, wherein said compound has the structure:

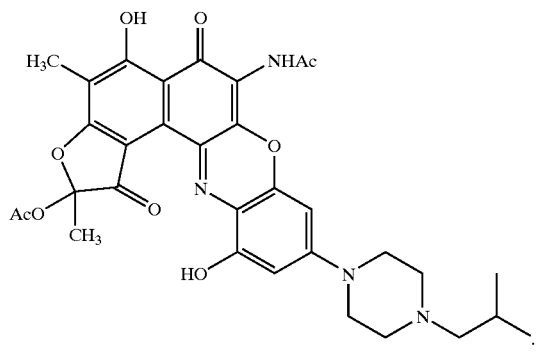

30. The method of claim 23, wherein said compound has the structure:

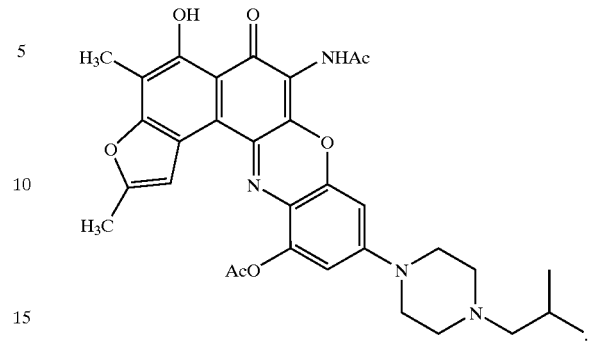

31. The method of claim 23, wherein said compound has the structure:

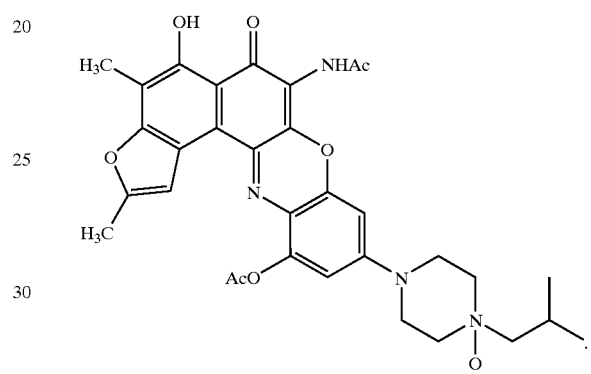

32. The method of claim 23, wherein said compound has the structure:

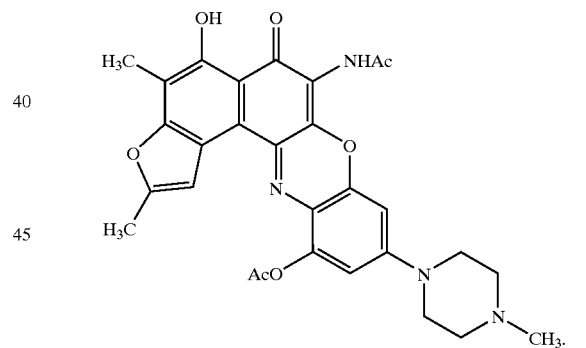

33. The method of claim 23, wherein said compound has the structure:

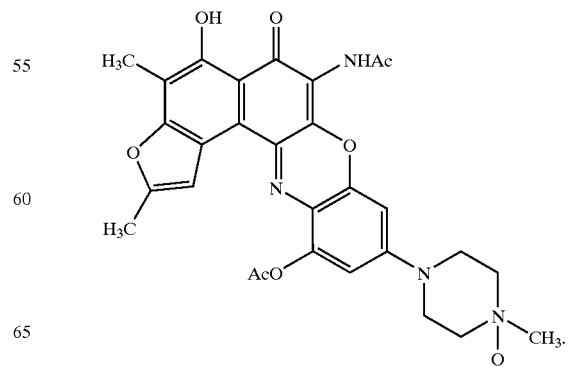

34. The method of claim 23, wherein said compound has the structure:

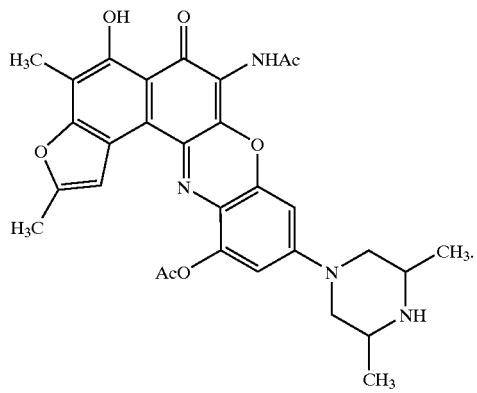

35. The method of claim 23, wherein said compound has the structure:

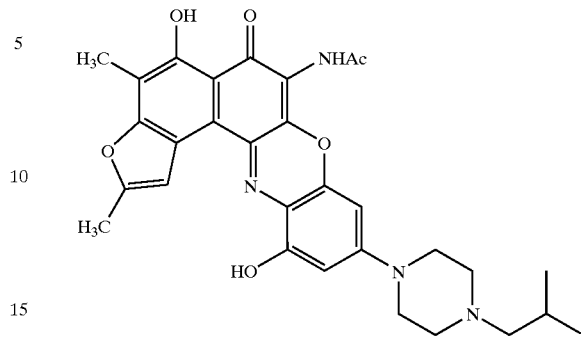

36. A method of enhancing the antibacterial activity of an antibacterial agent against bacteria, said method comprising:
   a. contacting the bacteria with the antibacterial agent; and
   b. contacting the bacteria with a compound of claim 1 in an amount effect to increase the antibacterial activity of the antibacterial agent.

* * * * *